US011702699B2

(12) United States Patent
Chun et al.

(10) Patent No.: US 11,702,699 B2
(45) Date of Patent: *Jul. 18, 2023

(54) DETECTION OF NUCLEOTIDE VARIATION ON TARGET NUCLEIC ACID SEQUENCE

(71) Applicant: SEEGENE, INC., Seoul (KR)

(72) Inventors: Jong Yoon Chun, Seoul (KR); Young Jo Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 663 days.

This patent is subject to a terminal disclaimer.

(21) Appl. No.: 14/893,676

(22) PCT Filed: Feb. 25, 2014

(86) PCT No.: PCT/KR2014/001529
§ 371 (c)(1),
(2) Date: Nov. 24, 2015

(87) PCT Pub. No.: WO2014/193071
PCT Pub. Date: Dec. 4, 2014

(65) Prior Publication Data
US 2016/0215340 A1 Jul. 28, 2016

Related U.S. Application Data

(60) Provisional application No. 61/827,966, filed on May 28, 2013.

(51) Int. Cl.
C12Q 1/68 (2018.01)
C12Q 1/6883 (2018.01)
(Continued)

(52) U.S. Cl.
CPC ......... *C12Q 1/6883* (2013.01); *C12Q 1/6827* (2013.01); *C12Q 1/6844* (2013.01); *C12Q 2600/156* (2013.01)

(58) Field of Classification Search
CPC .. C12Q 1/6883; C12Q 1/6844; C12Q 1/6827; C12Q 2600/156; C12Q 1/686
See application file for complete search history.

(56) References Cited

U.S. PATENT DOCUMENTS 5,691,142 A    11/1997   Dahlberg et al.
6,893,819 B1   5/2005    Sorge
(Continued)

FOREIGN PATENT DOCUMENTS

WO    2008102057 A1    8/2008
WO    2012096523 A2    7/2012
(Continued)

OTHER PUBLICATIONS

Kisaki et al. (J Clin Laboratory Anal, 2010, 24:85-91) (Year: 2010).*

(Continued)

Primary Examiner — Stephanie K Mummert
(74) Attorney, Agent, or Firm — Gianna Julian Arnold; Saul Ewing LLP

(57) ABSTRACT

The present invention relates to the detection of a nucleotide variation on a target nucleic acid sequence using an amplification blocker and a VD-PTOCE (Variation Detection by PTO Cleavage and Extension) assay. The present invention is significantly effective in the detection of a minority mutation in an excess of wild-type DNA.

13 Claims, 13 Drawing Sheets

Specification includes a Sequence Listing.

(51) Int. Cl.
*C12Q 1/6844* (2018.01)
*C12Q 1/6827* (2018.01)

(56) References Cited

U.S. PATENT DOCUMENTS

| | | | |
|---|---|---|---|
| 7,309,573 | B2 | 12/2007 | Sorge |
| 7,381,532 | B2 | 6/2008 | Sorge |
| 7,803,543 | B2 | 9/2010 | Chiou et al. |
| 7,932,039 | B2 * | 4/2011 | Agarwal .............. C12Q 1/6827 |
| | | | 435/6.1 |
| 8,153,772 | B2 * | 4/2012 | Brown ................... C07H 21/00 |
| | | | 536/23.1 |
| 8,206,929 | B2 | 6/2012 | Grow et al. |
| 9,840,739 | B2 * | 12/2017 | Chun ................... C12Q 1/6827 |
| 2004/0014105 | A1 * | 1/2004 | Schroeder .............. C12Q 1/686 |
| | | | 435/6.12 |
| 2005/0053957 | A1 * | 3/2005 | Rosenblum .......... C12Q 1/6827 |
| | | | 435/6.11 |
| 2007/0099211 | A1 * | 5/2007 | Aivazachvili ...... G01N 27/3277 |
| | | | 435/5 |
| 2008/0241838 | A1 | 10/2008 | Scaboo et al. |
| 2009/0023151 | A1 | 1/2009 | Dawson et al. |
| 2010/0129812 | A1 | 5/2010 | Yoo |

FOREIGN PATENT DOCUMENTS

| | | |
|---|---|---|
| WO | 2012134195 A2 | 10/2012 |
| WO | 20130133561 A1 | 9/2013 |

OTHER PUBLICATIONS

Senescau, A., et al.; Use of a Locked-Nucleic-Acid Oligomer in the Clamped-Probe Assay for Detection of a Minority Pfcrt K76T Mutant Population of Plasmodium falciparum; Journal of Clinical Microbiology, Jul. 2005, pp. 3304-3308.

Nagai, Y., et al.; Genetic Heterogeneity of the Epidermal Growth Factor Receptor in Non-Small Cell Lung Cancer Cell Lines Revealed by a Rapid and Sensitive Detection System, the Peptide Nucleic Acid-Locked Nucleic Acid PCR Clamp; Cancer Res, Aug. 15, 2005; vol. 65, No. 16, pp. 7276-7282.

Marras, S., et al.; Multiplex detection of single-nucleotide variations using molecular beacons; Genetic Analysis: Biomolecular Engineering, 1999, vol. 14, pp. 151-156.

Lyamichev, V., et al.; Polymorphism identification and quantitative detection of genomic DNA by invasive cleavage of oligonucleotide probes; Nature Biotechnology, Mar. 1999; vol. 17, pp. 292-296.

Olivier, M.; The Invader® assay for SNP genotyping; Mutat Res., Jun. 3, 2005, vol. 573, Nos. 1-2; pp. 103-110.

Ørum, H., et al.; Single base pair mutation analysis by PNA directed PCR clamping; Nucleic Acids Research, 1993, vol. 21, No. 23, pp. 5332-5336.

Luo, J., et al.; Detection of rare mutant K-ras DNA in a single-tube reaction using peptide nucleic acid as both PCR clamp and sensor probe; Nucleic Acids Research, 2006, vol. 34, No. 2, e12; pp. 1-7.

* cited by examiner

A. Probing and Tagging Oligonucleotide (PTO)

B. Capturing and Templating Oligonucleotide (CTO)

Hybridization

Match Template          Mismatch Template

Primer extension & Cleavage of PTO-NV

Hybridization of PTO-NV fragment to CTO

Extension of PTO-NV fragment & Detection

Extended duplex

(Optional) Melting analysis

Hybridization

Primer extension & Cleavage of PTO-NV

Hybridization of PTO-NV fragment to CTO & Extension

Hybridization of SO to extended strand & Detection

(Optional) Melting analysis

Hybridization

Primer extension & Cleavage of PTO-NV

Hybridization of PTO-NV fragment and HO to CTO

Extension of PTO-NV fragment & Cleavage of HO & Detection

Mutant 100%

Mutant 10%

Mutant 1%

Mutant 0.1%

Mutant 0%

NTC

-○-  With amplification blocker
-△-  Without amplification blocker

FIGURE 8B

| Amplification blocker [1] | Wild-type DNA (ng) | Mutant DNA (ng) | Mutant ratio [2] (%) | Tm [4] (°C) | -d(RFU)/dT [5] |
|---|---|---|---|---|---|
| + | 0 | 100 | 100 | 71.5 | 411.3 |
| - | 0 | 100 | 100 | 71.5 | 428.8 |
| + | 90 | 10 | 10 | 71.5 | 417.5 |
| - | 90 | 10 | 10 | 71.5 | 56.6 |
| + | 99 | 1 | 1 | 71.5 | 315.5 |
| - | 99 | 1 | 1 | - | - |
| + | 99.9 | 0.1 | 0.1 | 71.5 | 164.1 |
| - | 99.9 | 0.1 | 0.1 | - | - |
| + | 100 | 0 | 0 | - | - |
| - | 100 | 0 | 0 | - | - |
| + | 0 | 0 | NTC [3] | - | - |
| - | 0 | 0 | NTC [3] | - | - |

[1] Amplification blocker comprises LNA. Its nucleotide variation discrimination site has a nucleotide sequence complementary to wild-type DNA.
[2] Mutant ratio represent the ratios of a mutant and a wild-type BRAF (V600E) human genomic DNA in sample mixtures.
[3] NTC represents No Template Control.
[4] Tm represents melting temperature of the extended duplex formed in VD-PTOCE assay.
[5] RFU represents relative fluorescence units.

Mutant 100%

Mutant 10%

Mutant 1%

Mutant 0%

NTC

-○-  With amplification blocker
-△-  Without amplification blocker

FIGURE 9B

| Amplification blocker [1] | Wild-type DNA (ng) | Mutant DNA (ng) | Mutant ratio [2] (%) | Tm [4] (°C) | -d(RFU)/dT [5] |
|---|---|---|---|---|---|
| + | 0 | 100 | 100 | 63.5 | 121.3 |
| − | 0 | 100 | 100 | 63.5 | 120.0 |
| + | 90 | 10 | 10 | 63.5 | 93.4 |
| − | 90 | 10 | 10 | - | - |
| + | 99 | 1 | 1 | 63.5 | 41.6 |
| − | 99 | 1 | 1 | - | - |
| + | 100 | 0 | 0 | - | - |
| − | 100 | 0 | 0 | - | - |
| + | 0 | 0 | NTC [3] | - | - |
| − | 0 | 0 | NTC [3] | - | - |

[1] Amplification blocker comprises LNA. Its nucleotide variation discrimination site has a nucleotide sequence complementary to wild-type DNA.
[2] Mutant ratio represent the ratios of a mutant and a wild-type BRAF (V600E) human genomic DNA in sample mixtures.
[3] NTC represents No Template Control.
[4] Tm represents melting temperature of the extended strand/SO duplex formed in VD-PTOCE assay using SO.
[5] RFU represents relative fluorescence units.

Mutant 100%

Mutant 10%

Mutant 1%

Mutant 0.1%

Mutant 0%

NTC

-○-  With amplification blocker
-△-  Without amplification blocker

FIGURE 10B

| Amplification blocker [1] | Wild-type DNA (ng) | Mutant DNA (ng) | Mutant ratio [2] (%) | $C_T$ |
|---|---|---|---|---|
| + | 0 | 100 | 100 | 31.4 |
| - | 0 | 100 | 100 | 28.0 |
| + | 90 | 10 | 10 | 36.8 |
| - | 90 | 10 | 10 | 35.5 |
| + | 99 | 1 | 1 | 38.5 |
| - | 99 | 1 | 1 | - |
| + | 99.9 | 0.1 | 0.1 | 42.0 |
| - | 99.9 | 0.1 | 0.1 | - |
| + | 100 | 0 | 0 | - |
| - | 100 | 0 | 0 | - |
| + | 0 | 0 | NTC [3] | - |
| - | 0 | 0 | NTC [3] | - |

[1] Amplification blocker comprises LNA. Its nucleotide variation discrimination site has a nucleotide sequence complementary to wild-type DNA.
[2] Mutant ratio represent the ratios of a mutant and a wild-type BRAF (V600E) human genomic DNA in sample mixtures.
[3] NTC represents No Target Control.

SEQUENCE LISTING

```
<160> NUMBER OF SEQ ID NOS: 9

<210> SEQ ID NO 1
<211> LENGTH: 39
<212> TYPE: DNA
<213> ORGANISM: Artificial Sequence
<220> FEATURE:
<223> OTHER INFORMATION: BRAF-F
<220> FEATURE:
<221> NAME/KEY: misc_feature
<222> LOCATION: (25)..(29)
<223> OTHER INFORMATION: n denotes deoxyinosine

<400> SEQUENCE: 1
cttcataatg cttgctctga taggnnnnng agatctact                    39

<210> SEQ ID NO 2
<211> LENGTH: 38
<212> TYPE: DNA
<213> ORGANISM: Artificial Sequence
<220> FEATURE:
<223> OTHER INFORMATION: BRAF-R
<220> FEATURE:
<221> NAME/KEY: misc_feature
<222> LOCATION: (24)..(28)
<223> OTHER INFORMATION: n denotes deoxyinosine

<400> SEQUENCE: 2
```

```
atagcctcaa ttcttaccat ccannnnntg gatccaga                              38
```

<210> SEQ ID NO 3
<211> LENGTH: 49
<212> TYPE: DNA
<213> ORGANISM: Artificial Sequence
<220> FEATURE:
<223> OTHER INFORMATION: BRAF-PTO-NV

<400> SEQUENCE: 3

```
ggtggacttg cggtctgtag ctagaccaaa atcacctatt tttactgtg               49
```

<210> SEQ ID NO 4
<211> LENGTH: 17
<212> TYPE: DNA
<213> ORGANISM: Artificial Sequence
<220> FEATURE:
<223> OTHER INFORMATION: Amplification blocker

<400> SEQUENCE: 4

```
cagtgaaatc tcgatgg                                                   17
```

<210> SEQ ID NO 5
<211> LENGTH: 39
<212> TYPE: DNA
<213> ORGANISM: Artificial Sequence
<220> FEATURE:
<223> OTHER INFORMATION: BRAF-CTO-1

<400> SEQUENCE: 5

```
tttttttga gccagagtta tggtcaccgc aagtccacc                            39
```

<210> SEQ ID NO 6
<211> LENGTH: 39
<212> TYPE: DNA
<213> ORGANISM: Artificial Sequence
<220> FEATURE:
<223> OTHER INFORMATION: BRAF-CTO-2

<400> SEQUENCE: 6

```
tttttttga gccagagtta tggtcaccgc aagtccacc                            39
```

<210> SEQ ID NO 7
<211> LENGTH: 24
<212> TYPE: DNA
<213> ORGANISM: Artificial Sequence
<220> FEATURE:
<223> OTHER INFORMATION: BRAF-SO

<400> SEQUENCE: 7

```
tttttttgag ccagagttat ggtc                                           24
```

<210> SEQ ID NO 8
<211> LENGTH: 43
<212> TYPE: DNA
<213> ORGANISM: Artificial Sequence
<220> FEATURE:
<223> OTHER INFORMATION: BRAF-CTO-3

<400> SEQUENCE: 8

```
tccgtccgag ccagagtgat ggtcacctca ccgcaagtcc acc                      43
```

<210> SEQ ID NO 9
<211> LENGTH: 24
<212> TYPE: DNA
<213> ORGANISM: Artificial Sequence

```
<220> FEATURE:
<223> OTHER INFORMATION: BRAF-HO

<400> SEQUENCE: 9
gaccatcact ctggctcgga cgga                                              24
```

DETECTION OF NUCLEOTIDE VARIATION ON TARGET NUCLEIC ACID SEQUENCE

CROSS-REFERENCE TO RELATED APPLICATIONS

This application is a national stage application filed under 35 U.S.C. 371 of PCT/KR2014/001529, filed on Feb. 25, 2014, which claims priority to U.S. Patent Application No. 61/827,966, filed May 28, 2013, the entire contents of each of which are hereby incorporated in total by reference.

SEQUENCE LISTING

This application incorporates by reference the Sequence Listing contained in an ASCII text file named "361406_00027_SeqList.txt" submitted via EFS-Web. The text file was created on Nov. 22, 2015, and is 3 kb in size.

BACKGROUND OF THE INVENTION

Field of the Invention

The present invention relates to the detection of a nucleotide variation on a target nucleic acid sequence using an amplification blocker and a VD-PTOCE (Variation Detection by PTO Cleavage and Extension) assay.

Description of the Related Art

DNA hybridization is a fundamental process in molecular biology and is affected by ionic strength, base composition, length of fragment to which the nucleic acid has been reduced, the degree of mismatching, and the presence of denaturing agents. DNA hybridization-based technologies would be a very useful tool in specific nucleic acid sequence determination and clearly be valuable in clinical diagnosis, genetic research, and forensic laboratory analysis.

However, the conventional methods and processes depending mostly on hybridization are very likely to produce false positive results due to non-specific hybridization between probes and non-target sequences. Therefore, there remain problems to be solved for improving their reliability.

Besides probe hybridization processes, several approaches using additional enzymatic reactions, for example, TaqMan™ probe method, have been suggested.

In TaqMan™ probe method, the labeled probe hybridized with a target nucleic acid sequence is cleaved by a 5' nuclease activity of an upstream primer-dependent DNA polymerase, generating a signal indicating the presence of a target sequence (U.S. Pat. Nos. 5,210,015, 5,538,848 and 6,326,145). The TaqMan™ probe method suggests two approaches for signal generation: polymerization-dependent cleavage and polymerization-independent cleavage. In polymerization-dependent cleavage, extension of the upstream primer must occur before a nucleic acid polymerase encounters the 5'-end of the labeled probe. As the extension reaction continues, the polymerase progressively cleaves the 5'-end of the labeled probe. In polymerization-independent cleavage, the upstream primer and the labeled probe are hybridized with a target nucleic acid sequence in close proximity such that binding of the nucleic acid polymerase to the 3'-end of the upstream primer puts it in contact with the 5'-end of the labeled probe to release the label. In addition, the TaqMan™ probe method discloses that the labeled probe at its 5'-end having a 5'-tail region not-hybridizable with a target sequence is also cleaved to form a fragment comprising the 5'-tail region.

There have been reported some methods in which a probe having a 5'-tail region non-complementary to a target sequence is cleaved by 5' nuclease to release a fragment comprising the 5'-tail region.

For instance, U.S. Pat. No. 5,691,142 discloses a cleavage structure to be digested by 5' nuclease activity of DNA polymerase. The cleavage structure is exemplified in which an oligonucleotide comprising a 5' portion non-complementary to and a 3' portion complementary to a template is hybridized with the template and an upstream oligonucleotide is hybridized with the template in close proximity. The cleavage structure is cleaved by DNA polymerase having 5' nuclease activity or modified DNA polymerase with reduced synthetic activity to release the 5' portion non-complementary to the template. The released 5' portion is then hybridized with an oligonucleotide having a hairpin structure to form a cleavage structure, thereby inducing progressive cleavage reactions to detect a target sequence.

U.S. Pat. No. 7,381,532 discloses a process in which the cleavage structure having the upstream oligonucleotide with blocked 3'-end is cleaved by DNA polymerase having 5' nuclease activity or FEN nuclease to release non-complementary 5' flap region and the released 5' flap region is detected by size analysis or interactive dual label. U.S. Pat. No. 6,893,819 discloses that detectable released flaps are produced by a nucleic acid synthesis dependent, flap-mediated sequential amplification method. In this method, a released flap from a first cleavage structure cleaves, in a nucleic acid synthesis dependent manner, a second cleavage structure to release a flap from the second cleavage structure and the release flaps are detected. U.S. Pat. No. 7,309,573 disclose a method including formation of a released flap produced by a nucleic acid synthesis; extension of the released flap; cleavage of an oligonucleotide during extension of the flap and detection of a signal generated by the cleavage of the oligonucleotide.

By hybridization of fluorescence-labeled probes in a liquid phase, a plurality of target nucleic acid sequences may be simultaneously detected using even a single type of a fluorescent label by melting curve analysis. However, the conventional technologies for detection of target sequences by 5' nuclease-mediated cleavage of interactive-dual labeled probes require different types of fluorescent labels for different target sequences in multiplex target detection, which limits the number of target sequences to be detected due to limitation of the number of types of fluorescent labels.

U.S. Pat. Appln. Pub. 2008-0241838 discloses a target detection method using cleavage of a probe having a 5' portion non-complementary to a target nucleic acid sequence and hybridization of a capture probe. A label is positioned on the non-complementary 5' portion. The labeled probe hybridized with the target sequence is cleaved to release a fragment, after which the fragment is then hybridized with the capture probe to detect the presence of the target sequence. In this method, it is necessary that an uncleaved/intact probe is not hybridized with the capture probe. For that, the capture probe having a shorter length has to be immobilized onto a solid substrate. However, such a limitation results in lower efficiency of hybridization on a solid substrate and also in difficulties in optimization of reaction conditions.

Therefore, there remain long-felt needs in the art to develop novel approaches for detection of a target sequence, preferably multiple target sequences, in a liquid phase and on a solid phase by not only hybridization but also enzymatic reactions such as 5' nucleolytic reaction in a more convenient, reliable and reproducible manner. Furthermore, a novel target detection method not limited by the number of types of labels (particularly, fluorescent labels) is also needed in the art.

In the meantime, nucleotide variations are important in the research and clinical fields. Of them, single nucleotide polymorphisms (SNPs) are most commonly found in a human genome and serve as markers for disease-related loci and pharmacogenetics (Landegren et al., 1998; Roses, 2000). SNPs are found at the rate of approximately 1 per 1000 bp in a human genome and their total number is estimated about three millions. For the detection of nucleotide variations such as SNP, deletion, insertion and translocation, various allelic discrimination technologies have been reported.

The allele-specific TaqMan probe is designed such that it is hybridized only with perfectly matched target sequences in extension step of PCR. The TaqMan probe has a reporter molecule and a quencher molecule capable of quenching the fluorescent signal from the reporter molecule. The TaqMan probe hybridized with target sequences is digested by 5' nuclease activity of Taq DNA polymerase and the reporter molecule and the quencher molecule are separated to generate a target signal. For allelic discrimination, 13-20 mer probes conjugated with minor groove binder (MGB) are used (Livak, et al., Genet. Anal. 14:143-149(1999)). Since the allelic discrimination method using the TaqMan probe employs not only hybridization reaction but also enzymatic reactions of 5' nuclease activity, its specificity is enhanced. However, the method has serious troublesome such as difficulties in allelic-specific probe design and optimized reaction conditions which have to discriminate difference by one mismatch. In addition, the conjugate with MGB is one of troubleshootings in the allele-specific TaqMan probe.

PCR clamping methods are disclosed for detection of minority mutant population by preferential amplification of Mutant allele with PNA or LNA clamp. The representative PCR clamping method using PNA is disclosed in Henrik et al., *Nucleic Acid Research* 21:5332-5336(1993) and Luo et al., *Nucleic Acid Research* Vol. 34, No 2 e12 (2006). However, the PCR clamping methods are likely not to perfectly block amplification of the wild-type allele.

Therefore, there remain long-felt needs in the art to develop novel approaches for detection of a nucleotide variation in a more convenient, reliable and reproducible manner, which is capable of being free from shortcomings of the conventional technologies.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop novel approaches to detect a target nucleotide variation on a target nucleic acid in low-abundance with more improved accuracy and convenience, inter alia, in a multiplex manner. As a result, we have established novel protocols for detection of a target nucleotide variation on a target nucleic acid in low-abundance by improving a VD-PTOCE assay developed by the present inventors (see PCT/KR2013/001492). The present protocols are well adopted to liquid phase reactions as well as solid phase reactions, and ensure detection of multiple nucleotide variations in low-abundance with more improved accuracy and convenience.

Therefore, it is an object of this invention to provide a method for detecting a target nucleotide variation on a target nucleic acid sequence using an amplification blocker and a VD-PTOCE assay.

It is another object of this invention to provide a kit for detecting a target nucleotide variation on a target nucleic acid sequence using an amplification blocker and a VD-PTOCE assay.

Other objects and advantages of the present invention will become apparent from the detailed description to follow taken in conjugation with the appended claims and drawings.

BRIEF DESCRIPTION OF THE DRAWINGS

FIG. 8A and FIG. 8B represent the results of the improvement of minority detection limit by the AB-VD PTOCE of the present invention.

FIG. 9A and FIG. 9B represent the results of the improvement of minority detection limit by the AB-VD PTOCE of the present invention using SO.

FIG. 10A and FIG. 10B represent the results of the improvement of minority detection limit by the AB-VD PTOCE of the present invention using HO.

DETAILED DESCRIPTION OF THIS INVENTION

Figure 1:
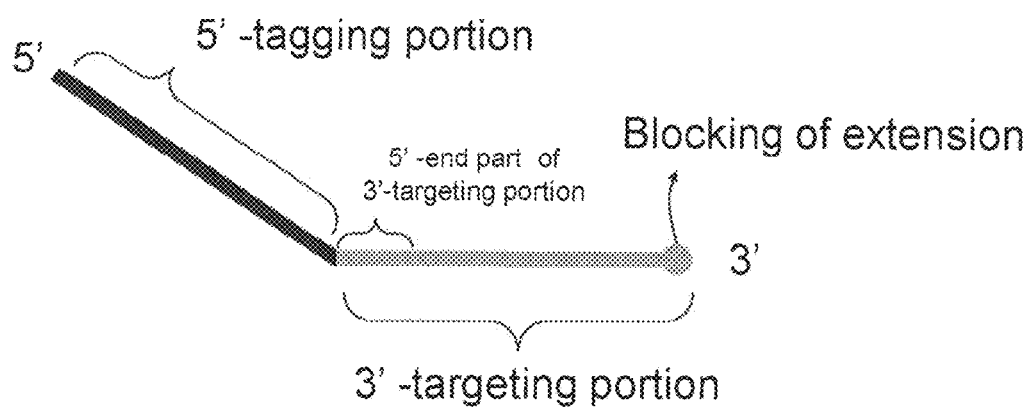
FIG. 1A shows the schematic structure of PTO (Probing and Tagging Oligonucleotide) used in PTO cleavage and extension assay (PTOCE assay). Preferably, the 3'-end of the PTO is blocked to prohibit their extension. The PTO-NV is a modification of the PTO, further comprising a nucleotide variation discrimination site comprising a complementary sequence to the target nucleotide variation on the target nucleic acid, positioned on a 5'-end part of the 3'-targeting portion.
FIG. 1B shows the schematic structure of CTO (Capturing and Templating Oligonucleotide) used in PTO cleavage and extension assay (PTOCE assay). Preferably, the 3'-end of the CTO is blocked to prohibit their extension.
Figure 1:
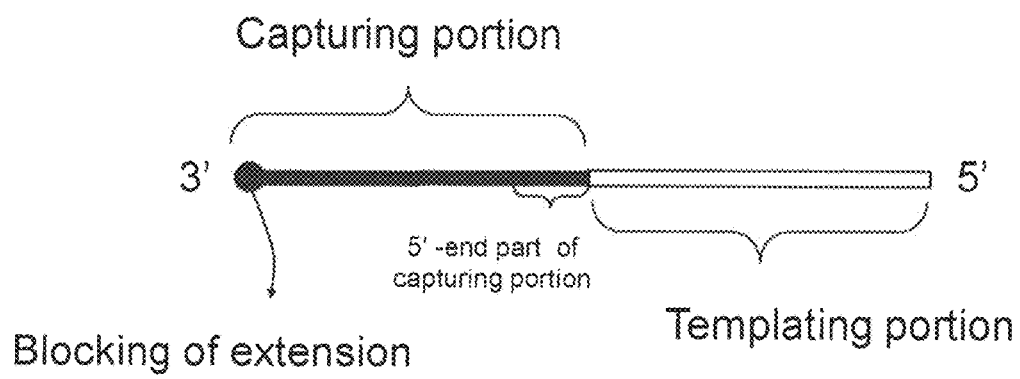

In one aspect of the present invention, there is provided a method for detecting a target nucleotide variation on a target nucleic acid sequence using an amplification blocker and a VD-PTOCE assay, comprising:

(a) hybridizing the target nucleic acid sequence with a primer pair comprising an upstream primer and a downstream primer for amplification of the target nucleic acid, the amplification blocker having the resistance to 5' nuclease cleavage and a PTO-NV (Probing and Tagging Oligonucleotide for Nucleotide Variation); wherein each of the upstream primer and the downstream primer comprises a hybridizing nucleotide sequence complementary to the target nucleic acid sequence; the amplification blocker comprises a complementary sequence to a non-target nucleotide variation different from the target nucleotide variation on the target nucleic acid sequence and the PTO-NV comprises (i) a 3'-targeting portion comprising a hybridizing nucleotide sequence complementary to the target nucleic acid sequence, (ii) a 5'-tagging portion comprising a nucleotide sequence non-complementary to the target nucleic acid sequence, and (iii) a nucleotide variation discrimination site, comprising a complementary sequence to the target nucleotide variation on the target nucleic acid, positioned on a 5'-end part of the 3'-targeting portion;

wherein the amplification blocker is hybridized with the target nucleic acid sequence having the non-target nucleotide variation and not hybridized with the target nucleic acid sequence having the target nucleotide variation; wherein the 3'-targeting portion of the PTO-NV is hybridized with the target nucleic acid sequence and the 5'-tagging portion the PTO-NV is not hybridized with the target nucleic acid sequence;

wherein the upstream primer is located upstream of the PTO-NV; the amplification blocker is located downstream of the upstream primer or the downstream primer; and the amplification blocker and the PTO-NV are located between the upstream primer and the downstream primer;

(b) contacting the resultant of the step (a) to an enzyme having a 5' nuclease activity under conditions for cleavage of the PTO-NV; wherein the upstream primer induces through its extended strand the cleavage of the PTO-NV by the enzyme having the 5' nuclease activity; wherein the hybridization of the amplification blocker with the target nucleic acid sequence having the non-target nucleotide variation inhibits the extension of the primer located upstream of the amplification blocker, thereby blocking the amplification of the target nucleic acid sequence having the non-target nucleotide variation;

wherein when the PTO-NV is hybridized with the target nucleic acid sequence having the target nucleotide variation complementary to the nucleotide variation discrimination site, the 5'-end part of the 3'-targeting portion forms a double strand with the target nucleic acid sequence to induce cleavage from a first initial cleavage site and a first fragment is released; wherein when the PTO-NV is hybridized with the target nucleic acid sequence having the non-target nucleotide variation non-complementary to the nucleotide variation discrimination site, the 5'-end part of the 3'-targeting portion does not form a double strand with the target nucleic acid sequence to induce cleavage from a second initial cleavage site located downstream of the first initial cleavage site and a second fragment is released; wherein the second fragment comprises an additional 3'-end portion allowing the second fragment different from the first fragment;

(c) hybridizing the fragment released from the PTO-NV with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO-NV and (ii) a templating portion comprising a nucleotide sequence non-complementary to the 5'-tagging portion and the 3'-targeting portion of the PTO-NV; wherein the first fragment or the second fragment released from the PTO-NV is hybridized with the capturing portion of the CTO;

(d) performing an extension reaction using the resultant of the step (c) and a template-dependent nucleic acid polymerase; wherein when the first fragment is hybridized with the capturing portion of the CTO, it is extended to form an extended strand comprising a extended sequence complementary to the templating portion of the CTO; wherein when the second fragment is hybridized with the capturing portion of the CTO, it is not extended; and (e) detecting the presence of the extended strand, whereby the presence of the extended strand indicates the presence of the target nucleotide variation.

The present inventors have made intensive researches to develop novel approaches to detect a target nucleotide variation on a target nucleic acid in low-abundance. As a result, we have established novel protocols for detection of a target nucleotide variation on a target nucleic acid in low-abundance by improving a VD-PTOCE assay developed by the present inventors (see PCT/KR2013/001492). The VD-PTOCE assay is a particular embodiment of a PTOCE assay developed by the present inventors (see WO 2012/096523) for detecting nucleotide variations. The present protocols are well adopted to liquid phase reactions as well as solid phase reactions, and ensure detection of multiple nucleotide variations in low-abundance with more improved accuracy and convenience.

The present invention is aimed to effective detection of a target nucleotide variation on a target nucleic acid in low-abundance by applying a preferential amplification of certain sequence using an amplification blocker to a VD-PTOCE assay using a PTO-NV (Probing and Tagging Oligonucleotide for Nucleotide Variation).

The present invention employs successive events followed by an amplification blocker and a PTO-NV hybridization; cleavage of PTO-NV (Probing and Tagging Oligonucleotide for Nucleotide Variation) and extension; formation of a nucleotide variation-dependent extended strand; and detection of the extended strand. Therefore, it is named as AB-VD PTOCE (Amplification Blocker-Involved Variation Detection by PTO Cleavage and Extension) assay.

Clinical samples frequently contain a low-amount of mutant allele in an excess of wild-type allele. The excess of wild-type allele can exhaust essential reagents during amplification process and tends to mask the mutant allele's signal. To overcome this problem, a multitude of methods have been suggested to selectively amplify mutant allele while suppressing the amplification of wild-type allele.

As representatives, the methods using oligonucleotides containing PNA or LNA as an amplification blocker have been reported (US 2004/0014105, U.S. Pat. Nos. 7,803,543, 8,206,929, H. Orum., Nucleic Acids Research 21:5332-5336 (1993) A. Senescau et al., Journal of Clinical Microbiology, 3304-3308(2005), Y. Nagai et al., Cancer Res 65:7276-7282 (2005), Henrik et al., Nucleic Acid Research 21:5332-5336 (1993) and Luo et al., Nucleic Acid Research Vol. 34, No 2 e12 (2006)).

In general, the amplification blockers are hybridized only with templates having perfectly complementary sequence to the amplification blockers under the same condition, which are designed not to be hybridized with templates having even single mismatch. The template hybridized with the amplification blocker inhibiting primer annealing or chain elongation is not amplified and only that not hybridized with the amplification blocker is amplified. Nucleic acid analogues such as PNA and LNA are useful as amplification blockers in the senses that they show significant $T_m$, differences for even a single base difference.

Where polymerases used have nuclease activity, the amplification blocker is required to possess the resistance to the nuclease activity.

Also, the methods usually demand additional probes for signal generation. The amplification blocker may have labels.

Where a nucleotide variation region on a target nucleic acid sequence has two distinct variants, the amplification blocker permits to effectively detect the variant of interest by amplifying the target nucleic acid sequence having the variant of interest but inhibiting amplification of the target nucleic acid sequence having the other variant. In particular, the amplification blocker is very useful in detection of low-abundant mutant allele in clinical samples containing excess of wild-type allele and low-abundant mutant allele.

However, it is noteworthy that the amplification of wild-type allele may be not completely prevented by the amplification blocker. According to the present invention combining two technologies, i.e., the amplification blocker and the VD-PTOCE assay using the PTO-NV, it is possible to detect a very low-abundant mutant allele that is not detectable in conventional methods The VD-PTOCE assay of the present invention uses the PTO-NV having the nucleotide variation discrimination site positioned on the 5'-end part of the 3'-targeting portion for selectivity of the PTO to a specific nucleotide variation (see FIG. 1). Where the PTO-NV is hybridized with the target nucleic acid sequence (i.e., match template) having the nucleotide variation complementary to the nucleotide variation discrimination site, the 5'-end part of the 3'-targeting portion forms a double strand with the match template; however, where the PTO-NV is hybridized with a target nucleic acid sequence (i.e., mismatch template) having a nucleotide variation non-complementary to the nucleotide variation discrimination site, the 5'-end part of the 3'-targeting portion does not form a double strand with the mismatch template.

In the present application, a target nucleic acid sequence having a nucleotide variation complementary to the nucleotide variation discrimination site of the PTO-NV is also described as "match template" for the PTO-NV. A target nucleic acid sequence having a nucleotide variation non-complementary to the nucleotide variation discrimination site of the PTO is also described as "mismatch template" for the PTO-NV.

Unless otherwise indicated, the terms "match template" and "mismatch template" used herein are determined with regard to the PTO-NV.

It is noteworthy that such distinct hybridization patterns on the nucleotide variation of interest are responsible for differences in initial cleavage sites of the PTO-NV, thereby producing two types of PTO-NV fragments to give signal differentiation depending on the presence of the nucleotide variation of interest.

A first fragment is generated by cleavage of hybrid between the PTO-NV and match template. A second fragment is generated by cleavage of hybrid between the PTO-NV and mismatch template. The second fragment comprises further nucleotides in its 3'-end portion than the first fragment.

The production of either the first fragment or the second fragment may be distinctly detected by an extension reaction on the CTO.

Generally, the hybridization between a 3'-end part of primers and a template is very crucial to extension of primers in a stringent condition. In the present invention, the first fragment and the second fragment each is hybridized with the same site of the CTO. As described above, the second fragment comprises the additional 3'-end portion compared with the first fragment. By adjusting hybridization conditions and a sequence of the CTO opposed to the additional 3'-end portion of the second fragment, only the first fragment may be permitted to extend.

The production of the extended strand by extension of the first fragment may be detected by a variety of methods.

Figure 2:
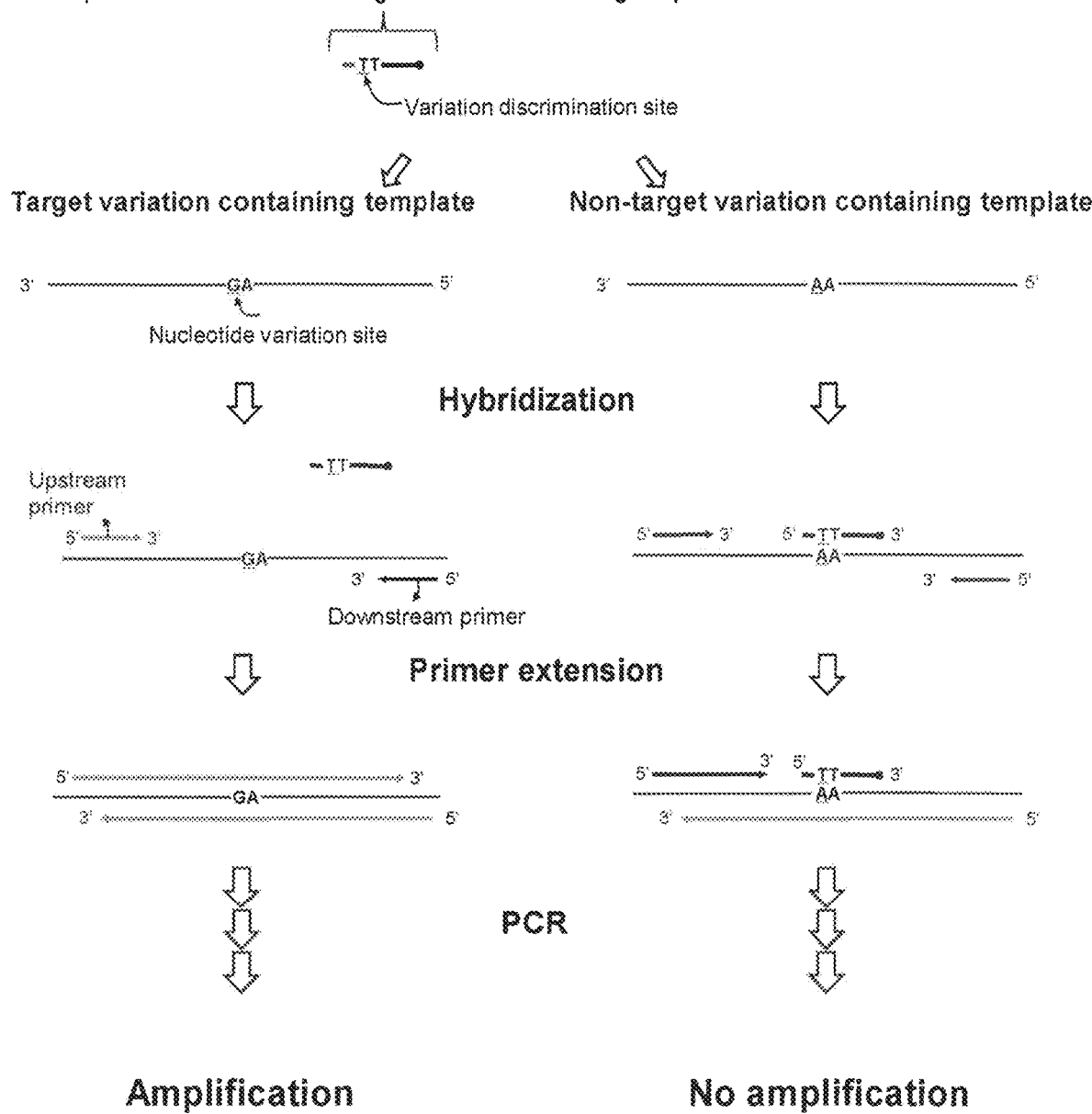
FIG. 2 schematically represents the selective amplification of a target nucleic acid sequence containing a target nucleotide variation (i.e., target variation containing template) by using an amplification blocker.
Figure 3:
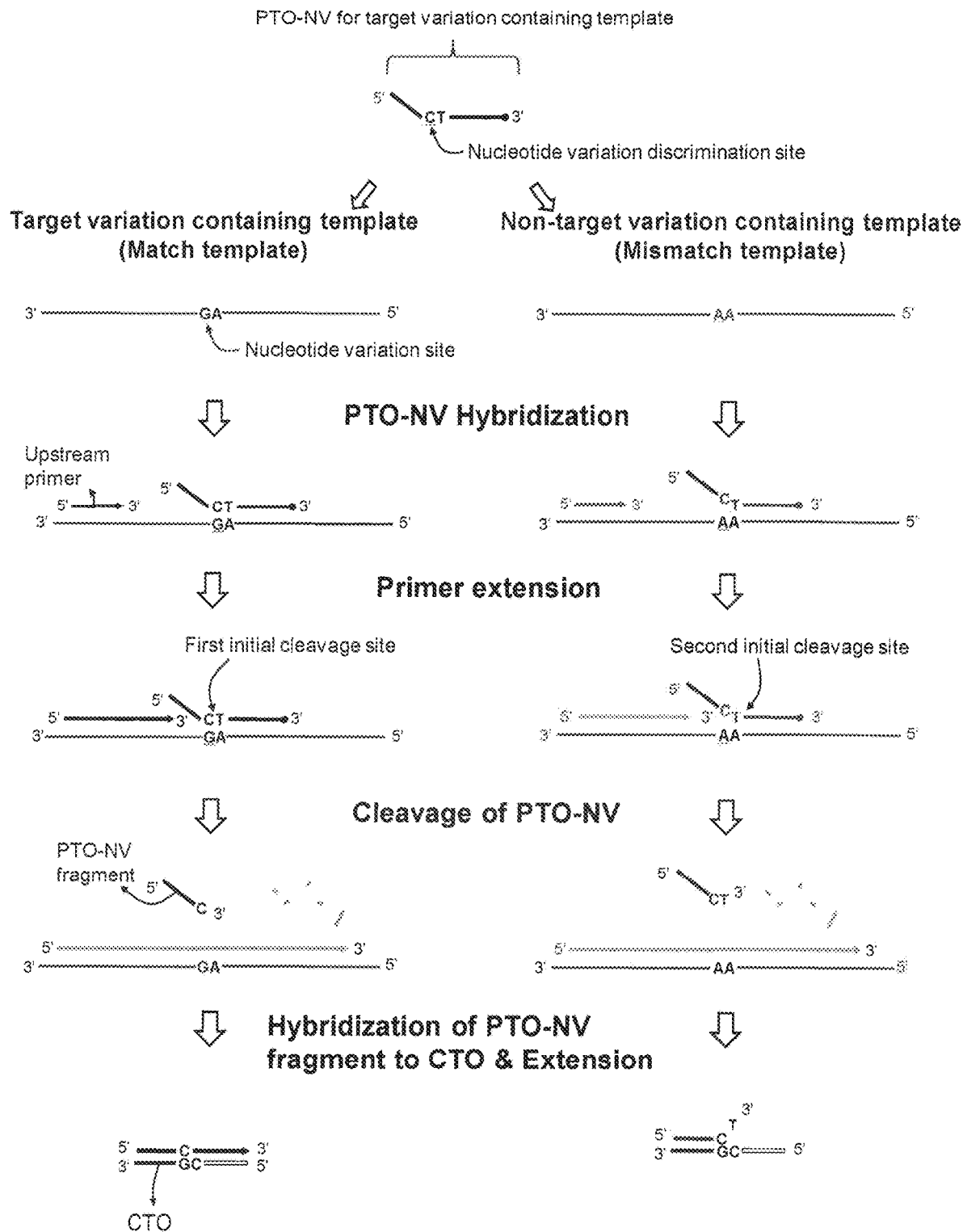
FIG. 3 schematically represents the selective detection of a target nucleotide variation by the AB-VD PTOCE of the present invention.

FIGS. 2 and 3 schematically represent an embodiment of this invention. FIGS. 2 and 3 are provided herein only for understanding the performance principle underlying the present invention. FIG. 2 represents selective amplification of the target variation containing template with no amplification of the non-target variation containing template due to the amplification blocker. FIG. 3 represents selective formation of the extended strand. Actually, the selective formation of the extended strand may also occur during the amplification of the target variation containing template. As exemplified in Example 3, a detectable signal may be observed after several amplification cycles.

In FIG. 2, the upstream primer and the downstream primer amplify the target variation containing template. However, the non-target variation containing template is not amplified due to the amplification blocker comprising a complementary sequence to a non-target nucleotide variation. In FIG. 3, the nucleotide variation discrimination site of the PTO-NV comprises a complementary sequence to the target nucleotide variation. The PTO-NV are hybridized with the target variation containing template (match template), and the PTO-NV is cleaved at a first initial cleavage site to form a first fragment, along with the extension of the upstream primer, thereby forming the extended strand on the CTO. On the other hand, the PTO-NV hybridized with the non-target variation containing template (mismatch template) is cleaved at a second initial cleavage site to form a second fragment, along with the extension of the upstream primer, whereby the extended strand on the CTO is not formed.

As represented in FIG. 3, the PTO-NV may be hybridized with the two target nucleic acid sequences each of which has a distinct variant. When the amount of the variant containing a non-target variation is significantly higher than that of the variant containing the target variation of interest, the PTO-NV is likely to be uselessly cleaved and consumed. The AB-VD PTOCE assay ensures the detection of multiple nucleotide variations in low-abundance with more improved accuracy and convenience by improving the VD-PTOCE assay with adopting an amplification blocker.

The AB-VD PTOCE assay will be described in more detail as follows:

Step (a): Hybridization of a Primer Pair, an Amplification Blocker and a PTO-NV with a Target Nucleic Acid Sequence According to the present invention, a target nucleic acid sequence is first hybridized with a primer pair, an amplification blocker and a PTO-NV (Probing and Tagging Oligonucleotide for Nucleotide Variation).

The term used herein "target nucleic acid", "target nucleic acid sequence" or "target sequence" refers to a nucleic acid sequence of interest for detection, which is annealed to or hybridized with a probe or primer under hybridization, annealing or amplifying conditions.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH.

The term used herein "probe" refers to a single-stranded nucleic acid molecule comprising a portion or portions that are substantially complementary to a target nucleic acid sequence.

Preferably, the probe and primer are single-stranded deoxyribonucleotide molecules. The probes or primers used in this invention may be comprised of naturally occurring dNMP (i.e., dAMP, dGM, dCMP and dTMP), modified nucleotide, or non-natural nucleotide. The probes or primers may also include ribonucleotides.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The term used "hybridizing" used herein refers to the formation of a double-stranded nucleic acid from complementary single stranded nucleic acids. The hybridization may occur between two nucleic acid strands perfectly matched or substantially matched with some mismatches. The complementarity for hybridization may depend on hybridization conditions, particularly temperature.

The hybridization of a target nucleic acid sequence with a primer pair, an amplification blocker and a PTO-NV may be carried out under suitable hybridization conditions routinely determined by optimization procedures. Conditions such as temperature, concentration of components, hybridization and washing times, buffer components, and their pH and ionic strength may be varied depending on various factors, including the length and GC content of oligonucleotide (primers and PTO) and the target nucleotide sequence. For instance, when a relatively short oligonucleotide is used, it is preferable that low stringent conditions are adopted. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N. Y. (1999).

There is no intended distinction between the terms "annealing" and "hybridizing", and these terms will be used interchangeably.

Each of the upstream primer and the downstream primer comprises a hybridizing nucleotide sequence complementary to a target nucleic acid sequence. The 3'-targeting portion of the PTO-NV comprises a hybridizing nucleotide sequence complementary to a target nucleic acid sequence. The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary", preferably perfectly complementary.

The 5'-tagging portion of the PTO-NV has a nucleotide sequence non-complementary to the target nucleic acid sequence. The templating portion of the CTO (Capturing and Templating Oligonucleotide) has a nucleotide sequence non-complementary to the 5'-tagging portion and the 3'-targeting portion of the PTO. The term "non-complementary" is used herein to mean that primers or probes are sufficiently non-complementary not to hybridize selectively to a target nucleic acid sequence under the designated annealing conditions or stringent conditions, encompassing the terms "substantially non-complementary" and "perfectly non-complementary", preferably perfectly non-complementary.

For example, the term "non-complementary" in conjunction with the 5'-tagging portion of the PTO-NV means that the 5'-tagging portion is sufficiently non-complementary not to hybridize selectively to a target nucleic acid sequence under the designated annealing conditions or stringent conditions, encompassing the terms "substantially non-complementary" and "perfectly non-complementary", preferably perfectly non-complementary.

The amplification blocker comprises a complementary sequence to a non-target nucleotide variation different from the target nucleotide variation on the target nucleic acid sequence. The amplification blocker is hybridized with the target nucleic acid sequence having the non-target nucleotide variation and not hybridized with the target nucleic acid sequence having the target nucleotide variation, thereby, the amplification blocker contributes the selective amplification of the target nucleic acid sequence having the target nucleotide variation.

The amplification blocker is located downstream of the upstream primer or the downstream primer; and the amplification blocker and the PTO-NV are located between the upstream primer and the downstream primer;

The term used herein "target nucleotide variation" with reference to a nucleotide variation present in a variation-occurring region on a target nucleic acid sequence means a nucleotide variation to be identified by the present invention. In the present method, a nucleotide variation discrimination site of PTO-NV comprises a complementary sequence to the target nucleotide variation on the target nucleic acid.

The term used herein "target nucleotide variation containing template" or "target variation containing template" means a target nucleic acid molecule comprising a nucleotide variation to be identified by the present invention.

The term used herein "non-target nucleotide variation" with reference to a nucleotide variation present in a variation-occurring region on a target nucleic acid sequence means other nucleotide variations than the target nucleotide variation.

The term used herein "non-target nucleotide variation containing template" or "non-target variation containing template" means a target nucleic acid molecule comprising a nucleotide variation other than the target nucleotide variation.

For example, in the detection of low-abundance mutant allele in an excess of wild-type allele by the present method, the wild-type allele is the target nucleic acid having non-target nucleotide variation and the mutant allele is the target nucleic acid having target nucleic variation. The term "nucleotide variation" includes a wild type and any mutant type at a particular location in a nucleic acid sequence.

In the present method, the amplification blocker comprises a complementary sequence to the non-target nucleotide variation. The non-target nucleotide variation present in the variation-occurring region may be one or more. In such case, the amplification blocker comprises a complementary sequence to the non-target nucleotide variation of which amplification is intended to be inhibited. For inhibition of a plurality of non-target nucleotide variations, a plurality of amplification blocker may be used.

The terms "target nucleotide variation" and "non-target nucleotide variation" are used herein to clearly and concisely indicate a nucleic acid molecule to be hybridized with the PTO-NV and the amplification blocker.

The amplification blocker comprising a complementary sequence to a non-target nucleotide variation whose amplification is intended to be inhibited is hybridized with a target nucleic acid sequence having the non-target nucleotide variation and inhibits the extension of a primer located upstream of the amplification blocker, thereby blocking the amplification of the target nucleic acid sequence.

Under the same conditions, the amplification blocker comprising a complementary sequence to a non-target nucleotide variation is not hybridized with a target nucleic acid sequence having a target nucleotide variation because of the presence of a mismatch sequence, thereby not blocking the amplification of the target nucleic acid sequence.

According to an embodiment, the amplification blocker comprising a complementary sequence to a wild-type DNA is hybridized with the wild-type DNA to inhibit the extension of primers, thereby suppressing the amplification of the wild-type DNA. The amplification blocker comprising a complementary sequence to a wild-type DNA is not hybridized with a mutant DNA, and the mutant DNA is amplified.

As the present invention employs the 5' nuclease activity, the amplification blocker is required to have the resistance to the 5' nuclease activity so as to prevent cleavage of the amplification blocker. In certain embodiment, at least a site of the amplification blocker attacked by the 5' nuclease activity is designed to have the resistance to the 5' nuclease activity.

In certain embodiment, the amplification blocker has the resistance to 5' nuclease cleavage. In certain embodiment, the amplification blocker is an oligonucleotide hybridizable with a nucleic acid sequence.

In an embodiment, the amplification blocker comprises a natural nucleoside/nucleotide, a nucleoside/nucleotide analogue or a combination thereof.

In an embodiment, the amplification blocker is an oligonucleotide having a compound resistant to 5' nuclease such as a minor groove binder.

According to an embodiment, the amplification blocker comprises nucleosides/nucleotides having a backbone resistant to the 5' nuclease activity.

The nucleosides/nucleotides with a backbone resistant to the 5' nuclease activity include any one known to one of skill in the art. For example, it includes various phosphorothioate linkages, phosphonate linkages, phosphoroamidate linkages and 2'-carbohydrates modifications. According to a more preferred embodiment, nucleotides having a backbone resistant to the 5' nuclease include phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage, aryl phosphoroamidate linkage, phosphoroselenate linkage, 2'-O-aminopropyl modification, 2'-O-alkyl modification, 2'-O-allyl modification, 2'-O-butyl modification, α-anomeric oligodeoxynucleotide and 1-(4'-thio-(3-D-ribofuranosyl) modification.

According to an embodiment, the amplification blocker comprises peptide nucleic acid (PNA), locked nucleic acid (LNA), Morpholino, glycol nucleic acid (GNA), threose nucleic acid (TNA), bridged nucleic acids (BNA), N3'-P5' phosphoramidate (NP) oligomers, minor groove binder-linked-oligonucleotides (MGB-linked oligonucleotides), phosphorothioate (PS) oligomers, $C_1$-$C_4$ alkylphosphonate oligomers, phosphoramidates, β-phosphodiester oligonucleotides, a-phosphodiester oligonucleotides or combination thereof.

In a particular embodiment, the amplification blocker has the resistance to the 5' nuclease and shows significant $T_m$ value changes by even a single mismatch, whose representative is an amplification blocker containing PNA or LNA.

The amplification blocker may be in any lengths. For example, the amplification blocker may be 5-100 nucleotides, 5-80 nucleotides, 5-50 nucleotides, 5-40 nucleotides, 5-30 nucleotides, 10-100 nucleotides, 10-80 nucleotides, 10-50 nucleotides, 10-40 nucleotides, 10-30 nucleotides, 15-100 nucleotides, 15-80 nucleotides, 15-50 nucleotides, 15-40 nucleotides, 15-30 nucleotides, 20-100 nucleotides, 20-80 nucleotides, 20-50 nucleotides, 20-40 nucleotides or 20-30 nucleotides in length.

According to an embodiment, the 3'-end of the amplification blocker is "blocked" to prohibit its extension.

The nucleotide variation discrimination site (i.e., a complementary region to the non-target nucleotide variation) of the amplification blocker to be opposite to the nucleotide variation region on the target nucleic acid sequence may be located on any site of the amplification blocker, so long as it inhibits the amplification of the target nucleic acid sequence having the non-target nucleotide variation but does not inhibit the amplification of the target nucleic acid sequence having the target nucleotide variation.

In certain embodiment, the nucleotide variation discrimination site of the amplification blocker may be located at its 5'-end portion, middle portion or 3'-end portion.

The amplification blocker is located downstream of the upstream primer or the downstream primer and the amplification blocker is located between the upstream primer and the downstream primer.

The distance between 5'-end of the amplification blocker and 3'-end of the primer located upstream thereof may be not less than 300, 200, 100, 50, 30, 20, 10, 5, 2 or 1 nucleotide.

In certain embodiment, the present invention is conducted in accordance with asymmetric PCR (Pierce K E et al., Methods Mol Med. Methods in Molecular Medicine 132: 65-85(2007)). Either the excess primer or limiting primer may be located upstream of the amplification blocker. Particularly, the excess primer may be located upstream of the amplification blocker.

The PTO-NV and the amplification blocker may be designed to locate on the same strand or different strands of the target nucleic acid sequence.

According to an embodiment, the nucleotide variation to be detected by the present invention is a substitution variation, a deletion variation or an insertion variation.

According to an embodiment, the target nucleic acid sequence having nucleotide variation(s) to be detected by the present invention includes the genes such as K-ras, H-ras, N-ras, p53 (TP53), CDKN2A (p16), PIC3K, PTEN, RB1, epidermal growth factor receptor gene, BRAF, BRCA1, BRCA2, STK11, and VHL; NF1, FBN1, MSH2, MLH1 (autosomal dominant disorder-associated gene); CFTR, Hemoglobin beta gene, HEXA, SMN1, VAPB (autosomal recessive disorder-associated gene); PHEX (X-linked dominant disorder-associated gene); factor VIII, dystrophin gene, CNGA 3, CNGB3, GNAT2, androgen receptor (AR) gene (X-linked recessive disorder-associated gene); USP9Y (Y-linked disorder-associated gene); MT-ND1, MT-ND4, MT-ND4L, MT-ND6 (mitochondrial disease-associated gene); the epithelial growth factor receptor (EGFR) gene which encodes EGFR in respect to the drug (gefitnib) for treatment of lung cancer, the multi-drug resistance-associated protein (MRP) gene encoding MRP in respect to the drug for treatment of ovarian cancer, and the lung resistance protein (LRP) gene in respect to the drug for treatment of ovarian cancer; and cagPAI, vacA, iceA, babA, erp, spvC, spuB, cnf1, cnf2, eaeA, eagg, einv, stx1, stx2, and vt2e etc. The term used herein "PTO-NV (Probing and Tagging Oligonucleotide for Nucleotide Variation)" means an oligonucleotide comprising (i) a 3'-targeting portion serving as a probe, (ii) a 5'-tagging portion with a nucleotide sequence non-complementary to the target nucleic acid sequence, and (iii) a nucleotide variation discrimination site, comprising a complementary sequence to the target nucleotide variation on the target nucleic acid, positioned on a 5'-end part of the 3'-targeting portion. The 5'-tagging portion is nucleolytically released from the PTO-NV after hybridization with the target nucleic acid sequence. The 5'-tagging portion and the 3'-targeting portion in the PTO-NV have to be positioned in a 5' to 3' order. The PTO-NV is schematically illustrated in FIGS. 1 and 3. The PTO-NV may be appreciated as one application form of the PTO for detection of nucleotide variations, which is constructed by introduction of the nucleotide variation discrimination site into the 5'-end part of the 3'-targting portion.

The PTO-NV comprises the nucleotide variation discrimination site comprising a complementary sequence to the nucleotide variation positioned on a 5'-end part of the 3'-targeting portion.

Where the PTO-NV is hybridized with the target nucleic acid sequence having the nucleotide variation complementary to the variation discrimination site, the 5'-end part of the 3'-targeting portion forms a double strand with the target nucleic acid sequence. Where the PTO-NV is hybridized with a target nucleic acid sequence having a nucleotide variation non-complementary to the variation discrimination site, the 5'-end part of the 3'-targeting portion does not form a double strand with the target nucleic acid sequence. Such distinct hybridization patterns on the nucleotide variation of interest are responsible for differences in cleavage sites of the PTO-NV, thereby producing two types of PTO-NV fragments to give signal differentiation depending on the presence of the nucleotide variation of interest. The 5'-end part of the 3'-targeting portion of the PTO-NV may be also described as a single strand-forming 5'-end portion of the 3'-targeting portion of the PTO-NV when hybridized with a target nucleic acid sequence having a nucleotide variation non-complementary to the variation discrimination site.

The nucleotide variation discrimination site positioned on a 5'-end part of the 3'-targeting portion of the PTO-NV comprises a complementary sequence to the nucleotide variation.

According to an embodiment, the nucleotide variation discrimination site is located within 10 nucleotides, more preferably 8 nucleotides, still more preferably 6 nucleotides, still much more preferably 4 nucleotides, 3 nucleotides, 2 nucleotides, 1 nucleotide or 0 nucleotide apart from the 5'-end of the 3'-targeting portion of the PTO-NV. Preferably, the nucleotide variation discrimination site is located at the 5'-end of the 3'-targeting portion of the PTO-NV.

The location of the nucleotide variation discrimination site may be determined in consideration of sequences to be detected, type of nucleases and reaction conditions.

The term "site" with reference to either nucleotide variation discrimination site of probes or nucleotide variation site on target sequences is used herein to encompass not only a single nucleotide but also a plurality of nucleotides.

Preferably, the hybridization in step (a) is preformed under stringent conditions that the 3'-targeting portion is hybridized with the target nucleic acid sequence and the 5'-tagging portion is not hybridized with the target nucleic acid sequence.

The PTO-NV does not require any specific lengths. For example, the length of the PTO-NV may be 15-150 nucleotides, 15-100 nucleotides, 15-80 nucleotides, 15-60 nucleotides, 15-40 nucleotides, 20-150 nucleotides, 20-100 nucleotides, 20-80 nucleotides, 20-60 nucleotides, 20-50 nucleotides, 30-150 nucleotides, 30-100 nucleotides, 30-80 nucleotides, 30-60 nucleotides, 30-50 nucleotides, 35-100 nucleotides, 35-80 nucleotides, 35-60 nucleotides, or 35-50 nucleotides. The 3'-targeting portion of the PTO-NV may be in any lengths so long as it is specifically hybridized with target nucleic acid sequences. For example, the 3'-targeting portion of the PTO-NV may be 10-100 nucleotides, 10-80 nucleotides, 10-50 nucleotides, 10-40 nucleotides, 10-30 nucleotides, 15-100 nucleotides, 15-80 nucleotides, 15-50 nucleotides, 15-40 nucleotides, 15-30 nucleotides, 20-100 nucleotides, 20-80 nucleotides, 20-50 nucleotides, 20-40 nucleotides or 20-30 nucleotides in length. The 5'-tagging portion may be in any lengths so long as it is specifically hybridized with the capturing portion of the CTO and then extended. For instance, the 5'-tagging portion of the PTO-NV may be 5-50 nucleotides, 5-40 nucleotides, 5-30 nucleotides, 5-20 nucleotides, 10-50 nucleotides, 10-40 nucleotides, 10-30 nucleotides, 10-20 nucleotides, 15-50 nucleotides, 15-40 nucleotides, 15-30 nucleotides or 15-20 nucleotides in length.

According to an embodiment, the PTO-NV is blocked at its 3'-end to prohibit its extension. The blocking may be achieved in accordance with conventional methods. For instance, the blocking may be performed by adding to the 3'-hydroxyl group of the last nucleotide a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

Alternatively, the PTO may be designed to have a hairpin structure.

The upstream primer is located upstream of the PTO-NV. The upstream primer induces through its extended strand the cleavage of the PTO-NV by an enzyme having a 5' nuclease activity.

In the present method, the term "the upstream primer" is determined with reference to the location of the PTO-NV and therefore the upstream primer is located upstream of the PTO-NV.

According to an embodiment, the upstream primer, the downstream primer and/or 5'-tagging portion of the PTO-NV have a dual priming oligonucleotide (DPO) structure developed by the present inventor. The oligonucleotides having the DPO structure show significantly improved target specificity compared with conventional primers and probes (see WO 2006/095981; Chun et al., Dual priming oligonucleotide system for the multiplex detection of respiratory viruses and SNP genotyping of CYP2C19 gene, *Nucleic Add Research*, 35:6e4C(2007)).

According to an embodiment, the 3'-targeting portion of the PTO-NV has a modified dual specificity oligonucleotide (mDSO) structure developed by the present inventor. The modified dual specificity oligonucleotide (mDSO) structure shows significantly improved target specificity compared with conventional probes (see WO 2011/028041).

The PTO-NV and the amplification blocker may be designed to locate on the same strand or different strands of the target nucleic acid sequence.

Figure 4:
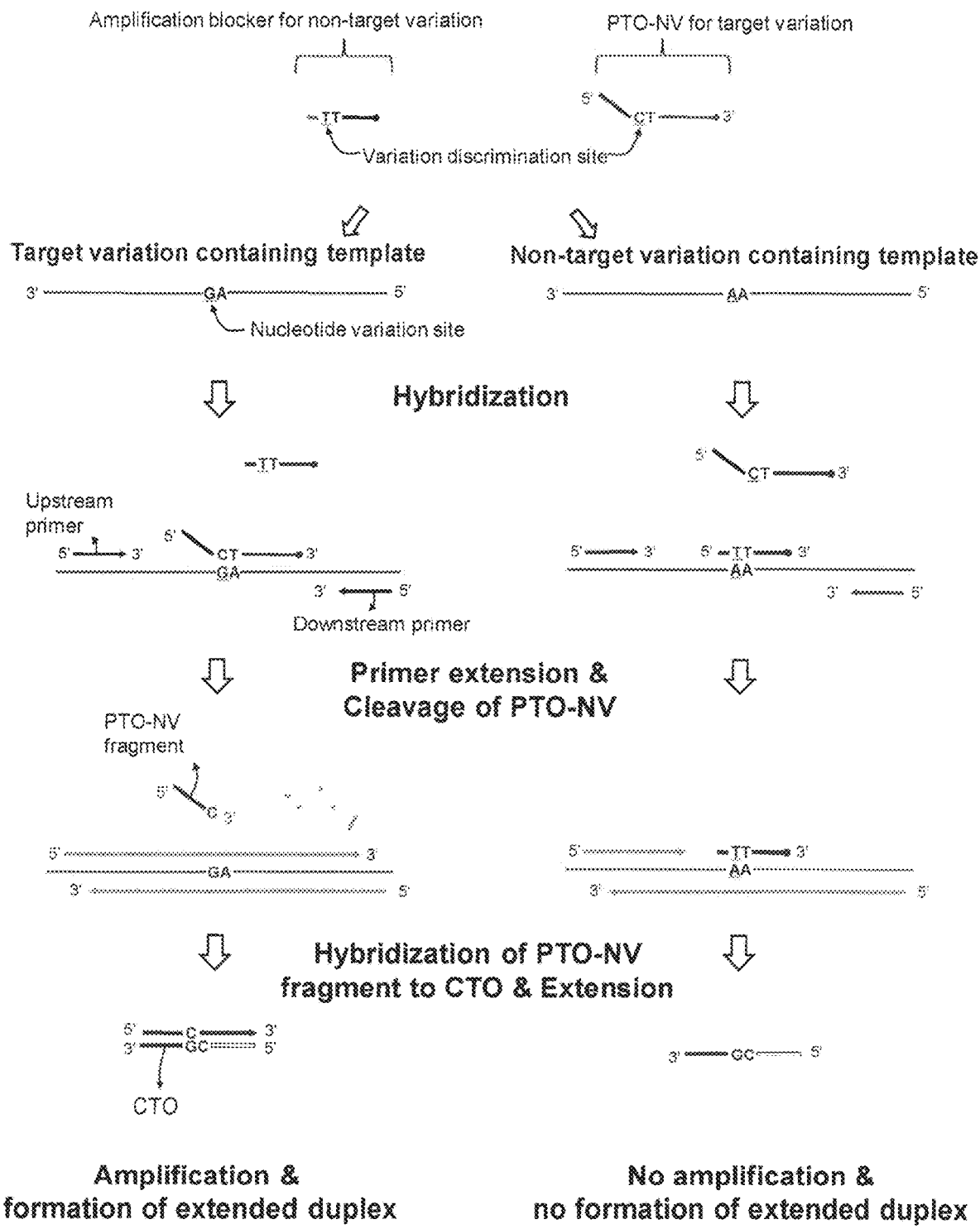
FIG. 4 schematically represents a co-working process of an amplification blocker and PTO-NV for detection of a target nucleotide variation on a target nucleic acid sequence. The amplification blocker and PTO-NV are designed to be located on the same strand of a target nucleic acid sequence.

In FIG. 4, the PTO-NV and the amplification blocker are located on the same strand of the target nucleic acid sequence. The nucleotide variation discrimination site of the PTO-NV comprises a complementary sequence to the target nucleotide variation on the target nucleic acid and the amplification blocker comprises a complementary sequence to the non-target nucleotide variation on the target nucleic acid. The PTO-NV is hybridized with target nucleotide variation containing template, and the PTO-NV is cleaved along with the extension of the upstream primer, forming the extended strand on the CTO. On the other hand, the amplification blocker is hybridized with the non-target nucleotide variation containing template, and the extension of the upstream primer is prevented by the amplification blocker. Furthermore, the existence of the amplification blocker on the non-target nucleotide variation containing template inhibits hybridization of the PTO-NV, preventing hybridization of PTO-NV with the non-target nucleotide variation containing template and its wasteful cleavage. By adjusting reaction conditions and sequences of the amplification blocker, the hybridization of the amplification blocker with the wild-type DNA may be rendered to be more favorable than that of the PTO-NV.

Alternatively, the PTO-NV and the amplification blocker may be designed to locate on different strands of the target nucleic acid sequence from each other.

Step (b): Release of a Fragment from the PTO-NV

Afterwards, the resultant of the step (a) is contacted to an enzyme having a 5' nuclease activity under conditions for cleavage of the PTO-NV. The upstream primer induces through its extended strand the cleavage of the PTO-NV by the enzyme having the 5' nuclease activity.

The term used herein "conditions for cleavage of the PTO-NV" means conditions sufficient to digest the PTO-NV hybridized with the target nucleic acid sequence by the enzyme having the 5' nuclease activity, such as temperature, pH, ionic strength, buffer, length and sequence of oligonucleotides and enzymes. For example, when Taq DNA polymerase is used as the enzyme having the 5' nuclease activity, the conditions for cleavage of the PTO include Tris-HCl buffer, KCl, $MgCl_2$ and temperature.

The hybridization of the amplification blocker with the target nucleic acid sequence having the non-target nucleotide variation inhibits the extension of the primer located upstream of the amplification blocker, thereby blocking the amplification of the target nucleic acid sequence having the non-target nucleotide variation.

Where the PTO-NV is hybridized with the target nucleic acid sequence (i.e., match template) having the target nucleotide variation complementary to the variation discrimination site, and the 5'-end part of the 3'-targeting portion forms a double strand with the target nucleic acid sequence to induce cleavage from a first initial cleavage site, a first fragment is released.

Where the PTO-NV is hybridized with a target nucleic acid sequence (i.e., mismatch template) having a non-target nucleotide variation non-complementary to the variation discrimination site, and the 5'-end part of the 3'-targeting portion does not form a double strand with the target nucleic acid sequence to induce cleavage from a second initial cleavage site located downstream of the first initial cleavage site, a second fragment is released; wherein the second fragment comprises an additional 3'-end portion allowing the second fragment different from the first fragment.

Where the target nucleic acid sequence is not present in a sample, the cleavage of the PTO-NV does not occur.

As such, differences in cleavage sites and types of PTO-NV fragments generated result in different extension patterns depending on the presence and absence of the nucleotide variation of interest on the target nucleic acid sequence, contributing to differential detection of the nucleotide variation on the target nucleic acid sequence.

An initial cleavage site of the PTO-NV is affected by the type of 5' nucleases, the hybridization site of the upstream primer and cleavage conditions.

An initial cleavage site by template dependent polymerase having 5' nuclease activity with extension of upstream primers is generally positioned in a 5' to 3' direction at an initial nucleotide of a double strand (i.e., bifurcation site) in structures including a single strand and a double strand or at 1-2 nucleotides apart from the initial nucleotide. By the cleavage reaction, fragments comprising the 5'-tagging portion and a part of the 3'-targeting portion are produced.

The term used herein "a first initial cleavage site" in conjunction with the PTO-NV means to a cleavage site of the PTO-NV being firstly cleaved when the PTO-NV is hybridized with the target nucleic acid sequence having the nucleotide variation complementary to the variation discrimination site. The term used herein "a second initial cleavage site" in conjunction with the PTO-NV means to a cleavage site of the PTO-NV being firstly cleaved when the PTO-NV is hybridized with a target nucleic acid sequence having a nucleotide variation non-complementary to the variation discrimination site.

The term used herein "a first fragment" refers to a fragment produced upon cleavage at the first initial cleavage site. The term is used interchangeably with "a first segment" and "a PTO-NV first fragment". The term herein "a second fragment" refers to a fragment produced upon cleavage at the second initial cleavage site. The term is used interchangeably with "a second segment" and "a PTO-NV second fragment".

Particularly, the first fragment and the second fragment each comprises the 5'-tagging portion or a part of the 5'-tagging portion.

The cleavage may successively occur after the cleavage of the first initial cleavage site (or the second initial cleavage site) depending on cleavage methods used. For instance, where 5' nuclease cleavage reaction together with extension of upstream primers is used, the initial cleavage site and its successive sequence are cleaved.

According to an embodiment, an initial cleavage site dependent on extension of upstream primers may be positioned in a 5' to 3' direction at an initial nucleotide of a double strand (i.e., bifurcation site).

As shown in FIG. 3 representing an example of the present invention, the nucleotide variation discrimination site is positioned at the 5'-end of the 5'-end part of the 3'-targeting portion of the PTO-NV. In such case, the first initial cleavage site is positioned immediately adjacent, in a 5' to 3' direction, to the 5'-end part of the 3'-targeting portion. In other words, the first initial cleavage site is positioned immediately adjacent, in a 3' direction, to the nucleotide variation discrimination site. The second initial cleavage site is generally positioned at 1 nucleotide apart, in a 3' direction, from the nucleotide variation discrimination site.

Alternatively, the nucleotide variation discrimination site may be positioned at 1 nucleotide apart from the 5'-end of the 5'-end part of the 3'-targeting portion. In such case, the first initial cleavage site is positioned immediately adjacent, in a 5' direction, to the nucleotide variation discrimination site. The second initial cleavage site is generally positioned at 1 nucleotide apart, in a 3' direction, from the nucleotide variation discrimination site.

According to an embodiment, the PTO-NV has a blocker portion containing a blocker resistant to cleavage by the enzyme having 5' nuclease activity and the blocker portion is used to control an initial cleavage site and/or successive cleavages.

According to an embodiment, the PTO-NV has a blocker portion containing as a blocker at least one nucleotide resistant to cleavage by the enzyme having 5' nuclease activity.

For example, to induce cleavage at the junction site between a hybridization portion of the PTO-NV (3'-targeting portion) and a non-hybridization portion (5'-tagging portion), the 5'-end part of 3'-targeting portion of PTO-NV may be blocked with blockers.

The number of blockers contained in the blocker portion may be not limited, preferably, 1-10, more preferably 2-10, still more preferably 3-8, most preferably 3-6 blockers. The blockers present in the PTO may be in a continuous or intermittent manner, preferably a continuous manner. The nucleotides as blockers with a backbone resistant to the 5' nuclease activity include any one known to one of skill in the art. For example, it includes various phosphorothioate linkages, phosphonate linkages, phosphoroamidate linkages and 2'-carbohydrates modifications. According to a more preferred embodiment, nucleotides having a backbone resistant to the 5' nuclease include phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage, aryl phosphoroamidate linkage, phosphoroselenate linkage, 2-O-aminopropyl modification, 2-O-alkyl modification, 2-O-allyl modification, 2'-O-butyl modification, α-anomeric oligodeoxynucleotide and 1-(4'-thio-β-D-ribofuranosyl) modification.

According to an embodiment, a nucleotide as a blocker includes LNA (locked nucleic acid).

The 5'-end part comprising the nucleotide variation discrimination site may be composed of a hybridizable sequence with the target nucleic acid sequence. Alternatively, the 5'-end part may partially comprise a non-hybridizable sequence. The introduction of a non-hybridizable sequence into the 5'-end part is very advantageous over single strand formation of the 5'-end part when the PTO-NV is hybridized with a target nucleic acid sequence having a nucleotide variation non-complementary to the nucleotide variation discrimination site.

According to an embodiment, the 5'-end part of the 3'-targeting portion of the PTO-NV comprises a non-base pairing moiety located within 1-10 nucleotides (more preferably 1-5 nucleotides) apart from the nucleotide variation discrimination site.

The non-base pairing moiety prevents the 5'-end part of the 3'-targeting portion from formation of a double strand with the target nucleotide sequence when the PTO-NV is hybridized with the target nucleic acid sequence having the nucleotide variation non-complementary to the variation discrimination site.

According to an embodiment, the non-base pairing moiety does not inhibit the formation of a double strand between the 5'-end part and the target nucleic acid sequence when the PTO-NV is hybridized with the target nucleic acid sequence having the nucleotide variation complementary to the nucleotide variation discrimination site.

According to an embodiment, the non-base pairing moiety enhances differentiation between the first initial cleavage site and the second initial cleavage site. For instance, where the cleavage sites do not become differentiated in a match template and mismatch template by difference in the variation discrimination site due to no difference in hybridization patterns of the 5'-end part of the 3'-targeting portion of the PTO-NV, the use of the non-base pairing moiety renders the hybridization patterns to become differentiated. In addition, even when the 5'-end part of the 3'-targeting portion of the PTO-NV shows different hybridization patterns in a match template and mismatch template by difference in the variation discrimination site, the use of the non-base pairing moiety enables to give much longer 3'-end portion of the second fragment than that of the first fragment, thereby completely preventing extension of the second fragment on the CTO.

The use of the non-base paring moiety may improve AB-VD PTOCE assay.

According to an embodiment, the use of the non-base pairing moiety (e.g., artificial mismatch nucleotide) enhances discrimination potential of the PTO-NV to nucleotide variations.

According to an embodiment, the differential recognition by the enzyme having the 5' nuclease activity between the first initial cleavage site and the second initial cleavage site is improved by the differentiation imposed by the non-base pairing moiety. The differentiation may be enhanced by the distance between the first initial cleavage site and the second initial cleavage site caused by the non-base pairing moiety. According to an embodiment, the non-base pairing moiety widens the distance between the first initial cleavage site and the second initial cleavage site.

According to an embodiment, the introduction of a non-base paring moiety sequence enables the second initial cleavage site to be adjusted.

Preferably, the non-base pairing moiety is located downstream of the nucleotide variation discrimination site.

For example, where a mismatch nucleotide as a non-base pairing moiety is introduced into a position 2 nucleotides apart, in a 3' direction, from the nucleotide variation discrimination site, the second initial cleavage site is adjusted to a position 2 nucleotides apart from the nucleotide variation discrimination site. In case of not using the mismatch nucleotide, the second initial cleavage site is positioned 1 nucleotide apart from the nucleotide variation discrimination site. That is to say, the non-base pairing moiety may widen the distance between the first initial cleavage site and the second initial cleavage site.

The non-base pairing moiety includes any moieties not forming a base pair between target nucleic acid sequences. Preferably, the non-base pairing moiety is (i) a nucleotide comprising an artificial mismatch base, a non-base pairing base modified to be incapable of base pairing or a universal base, (ii) a non-base pairing nucleotide modified to be incapable of base pairing, or (iii) a non-base pairing chemical compound.

For example, the non-base pairing moiety includes alkylene group, ribofuranosyl naphthalene, deoxy ribofuranosyl naphthalene, metaphosphate, phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage and aryl phosphoroamidate linkage. Conventional carbon spacers are also used as non-base pairing moieties.

Universal bases as non-base pairing moieties are useful in adjusting cleavage sites of the PTO-NV.

As base pairs containing universal bases such as deoxyinosine, 1-(2'-deoxy-beta-D-ribofuranosyl)-3-nitropyrrole and 5-nitroindole have a lower binding strength than those between natural bases, universal bases may be employed as non-base pairing moieties under certain hybridization conditions.

The non-base pairing moiety introduced into the 5'-end part has preferably 1-5, more preferably 1-2 moieties. A plurality of non-base pairing moieties in the 5'-end part may be present in a consecutive or intermittent manner. Preferably, the non-base pairing moiety has 2-5 consecutive moieties.

Preferably, the non-base pairing moiety is a non-base pairing chemical compound.

According to an embodiment, the nucleotide variation discrimination site and the non-base pairing moiety of the PTO-NV are located within 10 nucleotides (more preferably 8 nucleotides, 7 nucleotides, 6 nucleotides, 5 nucleotides, 4 nucleotides, 3 nucleotides, 2 nucleotides or 1 nucleotide, still more preferably 1 nucleotide) apart from the 5'-end of the 3'-targeting portion.

According to an embodiment, where PTO-NV is hybridized with the mismatch template, the second initial cleavage site comprises an initial site of a double strand (i.e., bifurcation site) in structures including a single strand and a double strand.

According to an embodiment, the PTO-NV has a blocker portion containing as a blocker at least one nucleotide resistant to cleavage by the enzyme having 5' nuclease activity and the blocker portion is positioned to control the initial cleavage site or prevent the cleavage at a site or sites.

The term "part" used in conjunction with the PTO-NV or CTO such as the part of the 5'-tagging portion of the PTO-NV, the 5'-end part of the 3'-targeting portion of the PTO-NV and the 5'-end part of the capturing portion of the CTO refers to a nucleotide sequence composed of 1-40, 1-30, 1-20, 1-15, 1-10 or 1-5 nucleotides, particularly, 1, 2, 3 or 4 nucleotides.

According to an embodiment, the enzyme having the 5' nuclease activity is DNA polymerase having a 5' nuclease activity or FEN nuclease, more preferably a thermostable DNA polymerase having a 5' nuclease activity.

A suitable DNA polymerase having a 5' nuclease activity in this invention is a thermostable DNA polymerase obtained from a variety of bacterial species, including *Thermus aquaticus* (Taq), *Thermus thermophilus* (Tth), *Thermus filiformis*, *Thermis flavus*, *Thermococcus literalis*, *Thermus antranikianii*, *Thermus caldophilus*, *Thermus chliarophilus*, *Thermus flavus*, *Thermus igniterrae*, *Thermus lacteus*, *Thermus oshimai*; *Thermus ruber*; *Thermus rubens*, *Thermus scotoductus*, *Thermus silvanus*, *Thermus* species Z05, *Thermus* species sps 17, *Thermus thermophilus*, *Thermotoga maritima*, *Thermotoga neapolitana*, *Thermosiphoafricanus*, *Thermococcus litoralis*, *Thermococcus barossi*, *Thermococcus gorgonarius*, *Thermotoga maritima*, *Thermotoga neapolitana*, *Thermosiphoafricanus*, *Pyrococcus woesei*, *Pyrococcus horikoshii*, *Pyrococcus abyssi*, *Pyrodictium occultum*, *Aquifex pyrophilus* and *Aquifex aeolieus*. Most preferably, the thermostable DNA polymerase is Taq polymerase.

According to an embodiment, a template-dependent polymerase is used for extension of the upstream and downstream primer.

According to an embodiment, the template-dependent polymerase for extension of the primers is identical to the enzyme having the 5' nuclease activity or the template-dependent polymerase for extension of the primers is different from the enzyme having the 5' nuclease activity.

Step (c): Hybridization of the Fragment Released from the PTO-NV with CTO

The fragment released from the PTO-NV is hybridized with a CTO (Capturing and Templating Oligonucleotide).

The CTO comprises in a 3' to 5' direction (i) a capturing portion comprising a nucleotide sequence complementary to the 5'-tagging portion or a part of the 5'-tagging portion of the PTO-NV and (ii) a templating portion comprising a nucleotide sequence non-complementary to the 5'-tagging portion and the 3'-targeting portion of the PTO-NV.

The first fragment and the second fragment have commonly a hybridizable sequence with the capturing portion of the CTO and thus one of them is hybridized with the CTO.

The second fragment produced when hybridized with the mismatch template comprises an additional 3'-end portion being different from the first fragment produced when hybridized with the match template.

According to an embodiment, the CTO has a sequence selected such that the CTO is not hybridized with the additional 3'-end portion of the second fragment to prevent the second fragment from extension when the second fragment is hybridized with the capturing portion of the CTO. For example, the sequence of the CTO may be selected such that the CTO has a mismatch nucleotide(s) opposed to the additional 3'-end portion of the second fragment. Alternatively, universal bases may be used instead of the mismatch nucleotide depending on reaction conditions.

The first initial cleavage site (or the second initial cleavage site) may not be fixed but rather multiple in a condition. For example, initial cleavage sites may be positioned in a 5' to 3' direction at an initial nucleotide of a double strand (i.e., bifurcation site) in structures including a single strand and a double strand and 1-2 nucleotides apart from the initial nucleotide. In such case, preferably, the sequence of the CTO is selected such that the shortest fragment released by the first initial cleavage is selectively extended in the present invention to generate the extended strand indicative of the presence of the nucleotide variation.

The templating portion of the CTO may comprise any sequence so long as it is non-complementary to the 5'-tagging portion and the 3'-targeting portion of the PTO-NV. Furthermore, the templating portion may comprise any sequence so long as it can be acted as a template for extension of the first fragment released from the PTO-NV.

The length of the CTO may be widely varied. For example, the CTO is 7-1000 nucleotides, 7-500 nucleotides, 7-300 nucleotides, 7-100 nucleotides, 7-80 nucleotides, 7-60 nucleotides, 7-40 nucleotides, 15-1000 nucleotides, 15-500 nucleotides, 15-300 nucleotides, 15-100 nucleotides, 15-80 nucleotides, 15-60 nucleotides, 15-40 nucleotides, 20-1000 nucleotides, 20-500 nucleotides, 20-300 nucleotides, 20-100 nucleotides, 20-80 nucleotides, 20-60 nucleotides, 20-40 nucleotides, 30-1000 nucleotides, 30-500 nucleotides, 30-300 nucleotides, 30-100 nucleotides, 30-80 nucleotides, 30-60 nucleotides or 30-40 nucleotides in length. The capturing portion of the CTO may have any length so long as it is specifically hybridized with the fragment released from the PTO. For example, the capturing portion of the CTO is 5-100 nucleotides, 5-60 nucleotides, 5-40 nucleotides, 5-30 nucleotides, 5-20 nucleotides, 10-100 nucleotides, 10-60 nucleotides, 10-40 nucleotides, 10-30 nucleotides, 10-20 nucleotides, 15-100 nucleotides, 15-60 nucleotides, 15-40 nucleotides, 15-30 nucleotides or 15-20 nucleotides in length. The templating portion of the CTO may have any length so long as it can act as a template in extension of the fragment released from the PTO. For example, the templating portion of the CTO is 1-900 nucleotides, 1-400 nucleotides, 1-300 nucleotides, 1-100 nucleotides, 1-80 nucleotides, 1-60 nucleotides, 1-40 nucleotides, 1-20 nucleotides, 2-900 nucleotides, 2-400 nucleotides, 2-300 nucleotides, 2-100 nucleotides, 2-80 nucleotides, 2-60 nucleotides, 2-40 nucleotides, 2-20 nucleotides, 5-900 nucleotides, 5-400 nucleotides, 5-300 nucleotides, 5-100 nucleotides, 5-80 nucleotides, 5-60 nucleotides, 5-40 nucleotides, 5-30 nucleotides, 10-900 nucleotides, 10-400 nucleotides, 10-300 nucleotides, 15-900 nucleotides, 15-100 nucleotides, 15-80 nucleotides, 15-60 nucleotides, 15-40 nucleotides or 15-20 nucleotides in length.

The 3'-end of the CTO may have a 3'-OH terminal. According to an embodiment, the 3'-end of the CTO is blocked to prohibit its extension. The non-extendible blocking of the CTO may be achieved in accordance with conventional methods.

The first fragment released from the PTO-NV is hybridized with the CTO, providing a form suitable in extension of the first fragment. Although an undigested PTO-NV is also hybridized with the capturing portion of the CTO through its 5'-tagging portion, its 3'-targeting portion is not hybridized to the CTO which prohibits the formation of an extended duplex.

The hybridization in the step (c) can be described in detail with referring to descriptions in the step (a).

Step (d): Extension of the Fragment

The extension reaction is carried out using the resultant of the step (c) and a template-dependent nucleic acid polymerase.

When the first fragment is hybridized with the capturing portion of the CTO, it is extended to form an extended strand comprising an extended sequence complementary to the templating portion of the CTO. When the second fragment is hybridized with the capturing portion of the CTO, it is not extended.

The term used herein "extended sequence" in conjunction with the extended strand means only a newly extended sequence which is a portion of the extended strand except the first fragment. The extended strand comprises the first fragment and the extended sequence.

In certain embodiment, the extended strand of the first fragment and the CTO form an extended duplex in the step (d).

The term used herein "extended duplex" means a duplex formed by extension reaction in which the first fragment hybridized with the capturing portion of the CTO is extended using the templating portion of the CTO as a template and the template-dependent nucleic acid polymerase.

The extended duplex has different $T_m$ value from that of the hybrid between the uncleaved PTO-NV and the CTO. Particularly, the extended duplex has higher $T_m$ value than the hybrid between the uncleaved PTO and the CTO.

The $T_m$ value of the extended duplex is adjustable by (i) a sequence and/or length of the first fragment, (ii) a sequence and/or length of the CTO or (iii) the sequence and/or length of the first fragment and the sequence and/or length of the CTO. The adjustable $T_m$ value of the extended duplex may be employed to give a target signal indicative of the presence of the extended strand by melting the extended duplex in the step (e).

The term used herein "$T_m$" refers to a melting temperature at which half a population of double stranded nucleic acid molecules are dissociated to single-stranded molecules. The $T_m$ value is determined by length and G/C content of nucleotides hybridized. The $T_m$ value may be calculated by conventional methods such as Wallace rule (R. B. Wallace, et al., *Nucleic Acids Research*, 6:3543-3547(1979)) and nearest-neighbor method (SantaLucia 3. Jr., et al., *Biochemistry*, 35:3555-3562(1996)); Sugimoto N., et al., *Nucleic Acids Res.*, 24:4501-4505(1996)).

According to an embodiment, the $T_m$ value refers to actual $T_m$ values under reaction conditions actually practiced.

The template-dependent nucleic acid polymerase used in the step (d) may include any nucleic acid polymerases, for example, Klenow fragment of *E. coli* DNA polymerase I, a thermostable nucleic acid polymerase and bacteriophage T7 DNA polymerase. Preferably, the polymerase is a thermostable DNA polymerase which may be obtained from a variety of bacterial species, including *Thermus aquaticus* (Taq), *Thermus thermophilus* (Tth), *Thermus filiformis*, *Thermis flavus*, *Thermococcus literalis*, *Thermus antranikianii Thermus caldophilus*, *Thermus chliarophilus*, *Thermus flavus*, *Thermus igniterrae*, *Thermus lacteus*, *Thermus oshimai*, *Thermus ruber; Thermus rubens*, *Thermus scotoductus*, *Thermus silvanus*, *Thermus* species Z05, *Thermus* species sps 17, *Thermus thermophilus*, *Thermotoga maritima*, *Thermotoga neapolitana*, *Thermosipho africanus*, *Thermococcus litoralis*, *Thermococcus barossi*, *Thermococcus gorgonarius*, *Thermotoga maritima*, *Thermotoga neapolitana*, *Thermosiphoafricanus*, *Pyrococcus furiosus*(Pfu), *Pyrococcus woesei*, *Pyrococcus honkoshii*, *Pyrococcus abyssi*, *Pyrodictium occultum*, *Aquifex pyrophilus* and *Aquifex aeolieus*. Most preferably, the template-dependent nucleic acid polymerase is Taq polymerase.

According to an embodiment, the enzyme having the 5' nuclease activity used in the step (b) is identical to the template-dependent nucleic acid polymerase used in the step (d). Particularly, the enzyme having the 5' nuclease activity used in the step (b), the template-dependent nucleic acid polymerase used for extension of the upstream primer and the template-dependent nucleic acid polymerase used in the step (d) are identical to one another.

Generally, the extension of primers may be controlled by hybridization between a 3'-end part of primers and a template. By adjusting primer sequences and reaction conditions (e.g. annealing temperature), the extension of primers having at their 3'-end part 1-3 mismatch nucleotides is allowable. Alternatively, the extension of primers may be allowable only when they have perfectly complementary sequence to target sequences.

According to an embodiment, the sequence of the CTO is selected that either the first fragment or the second fragment is selectively extended.

According to an embodiment, the extension of the fragment is carried out under conditions such that the extension does not occur even when a single mismatch is present at the 3'-end part of the fragment.

Step (e): Detection of the Extended Strand

The extended strand is detected after the extension reaction. The presence of the extended strand indicates the presence of the nucleotide variation complementary to the nucleotide discrimination site of the PTO-NV.

In the present invention, a hybrid between the uncleaved PTO-NV and the CTO or between the second fragment and the CTO may be formed. The differentiation the extended duplex from the hybrid between the uncleaved PTO-NV and the CTO described below may be also applied to the differentiation the extended duplex from the hybrid between the second fragment and the CTO.

Detection of Extended Duplex by Melting or Hybridization Analysis

According to an embodiment, the detection in the step (e) is carried out in accordance with the PTOCE assay comprising a melting analysis using signals from the extended duplex between the extended strand and the CTO (see WO 2012/096523).

According to an embodiment, the extended strand of the first fragment and the CTO form an extended duplex in the step (d); wherein the extended duplex has a $T_m$ value adjustable by (i) a sequence and/or length of the first fragment, (ii) a sequence and/or length of the CTO or (iii) the sequence and/or length of the first fragment and the sequence and/or length of the CTO; wherein the extended duplex provides a target signal by (i) at least one label linked to the first fragment and/or CTO, (ii) a label incorporated into the extended duplex during the extension reaction, (iii) at least one label linked to the first fragment and/or CTO and a label incorporated into the extended duplex during the extension reaction or (iv) intercalating label; and wherein the presence of the extended strand is detected by measuring the target signal from the extended duplex in accordance with a melting analysis or a hybridization analysis for the extended duplex.

The term used herein "melting analysis" means a method in which a target signal indicative of the presence of the extended strand is obtained by melting of the extended duplex, including a method to measure signals at two different temperatures, melting curve analysis, melting pattern analysis and melting peak analysis. Preferably, the melting analysis is a melting curve analysis.

According to an embodiment, the detection of the presence of the extended strand in the step (e) is carried out by a melting analysis in which the extended duplex is melted over a range of temperatures to give a target signal indicative of the presence of the extended strand.

Alternatively, the detection of the presence of the extended strand in the step (e) is carried out by a hybridization analysis. Preferably, the detection of the presence of the extended strand in the step (e) is carried out by a hybridization analysis in which the extended duplex is melted and the resultant is hybridized over a range of temperatures to give a target signal indicative of the presence of the extended strand.

According to an embodiment, the melting of the step (e) is followed by hybridization to give the target signal indicative of the presence of the extended strand. In that case, the presence of the extended strand is detected by hybridization curve analysis.

The melting curve or hybridization curve may be obtained by conventional technologies, for example, as described in U.S. Pat. Nos. 6,174,670 and 5,789,167, Drobyshev et al, Gene 188: 45(1997); Kochinsky and Mirzabekov *Human Mutation* 19:343(2002); Livehits et al *J. Biomol. Structure Dynam.* 11:783(1994); and Howell et al *Nature Biotechnology* 17:87(1999). For example, a melting curve or hybridization curve may consist of a graphic plot or display of the variation of the output signal with the parameter of hybridization stringency. Output signal may be plotted directly against the hybridization parameter. Typically, a melting curve or hybridization curve will have the output signal, for example fluorescence, which indicates the degree of duplex structure (i.e. the extent of hybridization), plotted on the Y-axis and the hybridization parameter on the X axis.

A plot of the first derivative of the fluorescence vs. temperature, i.e., a plot of the rate of change in fluorescence vs. temperature (dF/dT vs. T) or (−dF/dT vs. T) provides melting peak.

The step (e) performed in accordance with the melting or hybridization analysis will be described in detail with varying a labeling system as follows:

(i) Label Linked to the First Fragment and/or the CTO

According to an embodiment, the target signal is provided by at least one label linked to the first fragment and/or the CTO. As the extended duplex is formed between the first fragment and CTO, either the label on the first fragment or on the CTO is present on the extended duplex, providing the target signal in the melting step.

The label includes an interactive dual label and a single label.

(i-1) Interactive Dual Label

As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent.

In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent. The donor molecule and the acceptor molecule may be described as a reporter molecular and a quencher molecule in the present invention, respectively. Interactive dual label includes the label pair providing detectable signal based on contact-mediated quenching (Salvatore et al., Nucleic Acids Research, 2002 (30) no. 21 e122 and Johansson et al., J. AM. CHEM. SOC 2002 (124) pp 6950-6956). In the present invention, the interactive label system includes any or all cases inducing signal changes by interaction between at least two molecules (e.g. dyes).

Particularly, the signal indicative of the presence of the extended strand (i.e., the presence of the target nucleic acid sequence) is generated by interactive label systems, more preferably the FRET label system (i.e., interactive dual label system).

First Embodiment Intrastrand Interactive-Dual Label

Figure 5:
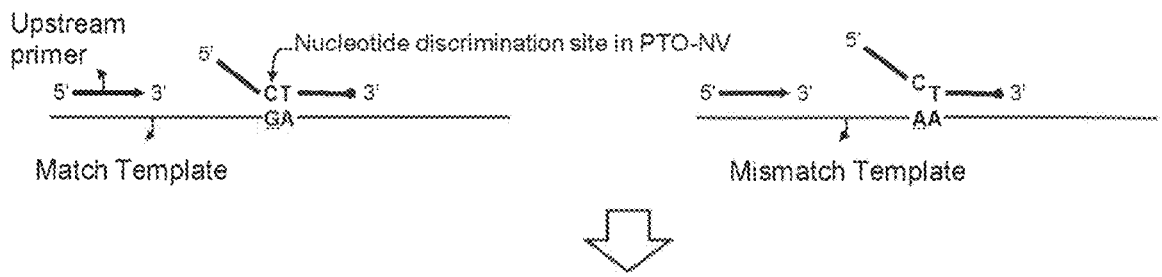
FIG. 5 schematically represents the selective detection of a target nucleotide variation by the AB-VD PTOCE of the present invention using the CTO labeled with an interactive dual label.
Figure 5:
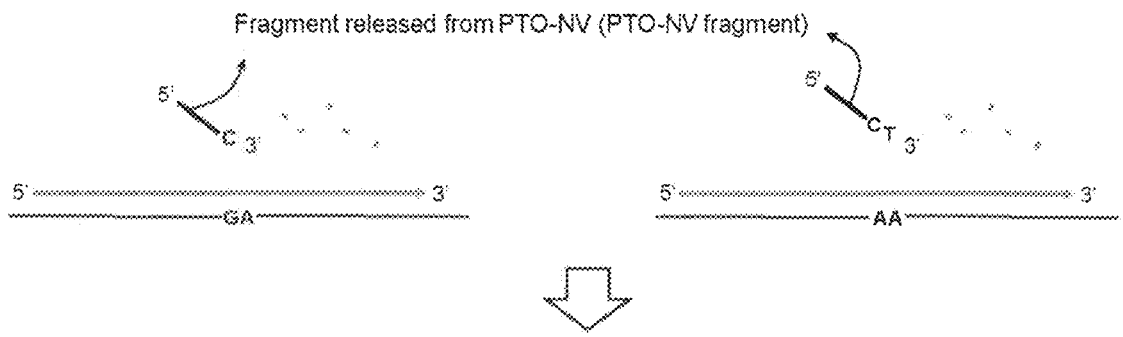
Figure 5:
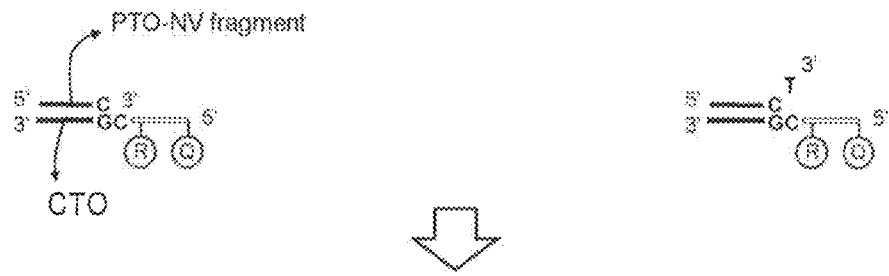
Figure 5:
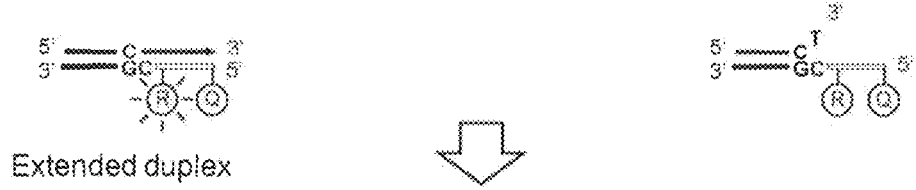
Figure 5:

In a first embodiment of an interactive dual label system, the first fragment or the CTO has an interactive dual label comprising a reporter molecule and a quencher molecule; wherein the melting of the extended duplex in the step (e) induces change of a signal from the interactive dual label to give the target signal in the step (e). The first embodiment of the interactive dual label system is illustrated in FIG. 5. The first embodiment is named as an intrastrand interactive-dual label.

First Embodiment-1 Intrastrand Interactive-Dual Label on the CTO

The exemplified embodiment is described with referring to FIG. 5. The templating portion of the CTO has a reporter molecule and a quencher molecule. The PTO-NV hybridized with the target nucleic acid sequence is digested to release the first fragment and the first fragment is hybridized with the capturing portion of the CTO and extended to form the extended duplex.

When the extended duplex is formed in the step (d), the reporter molecule and the quencher molecule on the CTO are conformationally separated to allow the quencher molecule to unquench the signal from the reporter molecule;

wherein when the extended duplex is melted in the step (e), the reporter molecule and the quencher molecule are conformationally adjacent to each other to allow the quencher molecule to quench the signal from the reporter molecule, such that the target signal is given to indicate the presence of the extended strand in the step (e).

The expression used herein "the reporter molecule and the quencher molecule are conformationally adjacent" means that the reporter molecule and the quencher molecule are three-dimensionally adjacent to each other by a conformational structure of the first fragment or CTO such as random coil and hairpin structure.

The expression used herein "the reporter molecule and the quencher molecule are conformationally separated" means that the reporter molecule and the quencher molecule are three-dimensionally separated by change of a conformational structure of the first fragment or CTO upon the formation of a double strand.

Preferably, the target signal given in the step (e) includes melting curve, a melting pattern or a $T_m$ value that is obtained by measuring change of the fluorescent signal generated in the step (d).

According to an embodiment, the reporter molecule and the quencher molecule may be located at any site on the CTO, so long as the signal from the reporter molecule is quenched and unquenched depending on melting of the extended duplex.

According to an embodiment, the reporter molecule and the quencher molecule both are linked to the templating portion or to the capturing portion of the CTO.

According to an embodiment, the reporter molecule and the quencher molecule are positioned at 5'-end and 3'-end of CTO.

According to an embodiment, one of the reporter molecule and the quencher molecule on the CTO is located at its 5'-end or at 1-5 nucleotides apart from its 5'-end and the other is located to quench and unquench the signal from the reporter molecule depending on conformation of CTO According to an embodiment, one of the reporter molecule and the quencher molecule on the CTO is located at its 3'-end or at 1-5 nucleotides apart from its 3'-end and the other is located to quench and unquench the signal from the reporter molecule depending on conformation of CTO.

According to an embodiment, the reporter molecule and the quencher molecule are positioned at no more than 80 nucleotides, more preferably no more than 60 nucleotides, still more preferably no more than 30 nucleotides, still much more preferably no more than 25 nucleotides apart from each other. According to an embodiment, the reporter molecule and the quencher molecule are separated by at least 4 nucleotides, more preferably at least 6 nucleotides, still more preferably at least 10 nucleotides, still much more preferably at least 15 nucleotides.

In the present invention, a hybrid between the uncleaved PTO-NV and the CTO may be formed.

Where the templating portion of the CTO is labeled with an interactive dual label as shown in FIG. 5, a signal change from the label on the hybrid between the uncleaved PTO-NV and the CTO is not induced. Therefore, the hybrid does not provide a non-target signal.

Where the capturing portion of the CTO is labeled with an interactive dual label, the hybrid between the uncleaved PTO and the CTO provides a non-target signal in the melting step. In this case, the difference in $T_m$ values of the extended duplex and the hybrid permits to discriminate the target signal of the extended duplex from the non-target signal of the hybrid.

First Embodiment-2 Intrastrand Interactive-Dual Label on the PTO-NV

The 5'-tagging portion of the PTO-NV may have a reporter molecule and a quencher molecule. The PTO-NV hybridized with the target nucleic acid sequence is digested to release the first fragment comprising the 5'-tagging portion with the reporter molecule and the quencher molecule. The first fragment is hybridized with the capturing portion of the CTO.

When the extended duplex is formed in the step (d), the reporter molecule and the quencher molecule on the first fragment are conformationally separated to allow the quencher molecule to unquench the signal from the reporter molecule; wherein when the extended duplex is melted in the step (e), the reporter molecule and the quencher molecule are conformationally adjacent to each other to allow the quencher molecule to quench the signal from the reporter molecule, such that the target signal is given to indicate the presence of the extended strand in the step (e).

According to an embodiment, the reporter molecule and the quencher molecule may be located at any site on the first fragment, so long as the signal from the reporter molecule is quenched and unquenched depending on melting of the extended duplex.

According to an embodiment, one of the reporter molecule and the quencher molecule on the first fragment is located at its 5'-end or at 1-5 nucleotides apart from its 5'-end and the other is located to quench and unquench the signal from the reporter molecule depending on conformation of the first fragment.

According to an embodiment, the reporter molecule and the quencher molecule are positioned at no more than 50 nucleotides, more preferably no more than 40 nucleotides, still more preferably no more than 30 nucleotides, still much more preferably no more than 20 nucleotides apart from each other. According to an embodiment, the reporter molecule and the quencher molecule are separated by at least 4 nucleotides, more preferably at least 6 nucleotides, still more preferably at least 10 nucleotides, still much more preferably at least 15 nucleotides.

The hybrid between the uncleaved PTO-NV and the CTO may provide a non-target signal in the melting step. In this case, the difference in $T_m$ values of the extended duplex and the hybrid permits to discriminate the target signal of the extended duplex from the non-target signal of the hybrid.

Second Embodiment Interstrand Interactive-Dual Label

In the second embodiment of the interactive label system, the first fragment has one of an interactive dual label comprising a reporter molecule and a quencher molecule and the CTO has the other of the interactive dual label; wherein the melting of the extended duplex in the step (e) induces change of a signal from the interactive dual label to give the target signal in the step (e).

For example, when the extended duplex is formed in the step (d), the signal from the reporter molecule linked to the CTO is quenched by the quencher molecule linked to the PTO-NV. When the extended duplex is melted in the step (e), the reporter molecule and the quencher molecule are separated to allow the quencher molecule to unquench the signal from the reporter molecule, such that the target signal is given to indicate the presence of the extended strand in the step (e).

Particularly, the target signal given in the step (e) includes a melting curve, a melting pattern or a $T_m$ value that is obtained by measuring change of the fluorescent signal from the interactive dual label.

The reporter molecule and the quencher molecule may be located at any site of the first fragment and the CTO, so long as the signal from the reporter molecule is quenched by the quencher molecule in the extended duplex.

According to an embodiment, the reporter molecule or the quencher molecule on the PTO-NV fragment is located at the 5'-end of the 5'-tagging portion.

According to an embodiment, the reporter molecule or the quencher molecule on the CTO is located at its 3'-end.

The hybrid between the uncleaved PTO and the CTO may provide a non-target signal in the melting step. In this case, the difference in $T_m$ values of the extended duplex and the hybrid permits to discriminate the target signal of the extended duplex from the non-target signal of the hybrid.

The reporter molecule and the quencher molecule useful in the present invention may include any molecules known in the art. Examples of those are: Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™(531), Calcium Green™ (533), TO-PRO™-1 (533), TOTO1 (533), JOE (548), BODIPY530/550 (550), DiI (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™(576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red(615), Nile Red (628), YO-PRO™-3 (631), YOYO™-3 (631), R-phycocyanin (642), C-Phycocyanin (648), TO-PRO™-3 (660), TOTO3 (660), DiD DilC(5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer. Particularly, the reporter molecule and the quencher molecule include JOE, FAM, TAMRA, ROX and fluorescein-based label.

Suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, N.Y. 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, $6^{th}$ Edition (Molecular Probes, Eugene, Oreg., 1996) U.S. Pat. Nos. 3,996,345 and 4,351,760.

It is noteworthy that a non-fluorescent black quencher molecule capable of quenching a fluorescence of a wide range of wavelengths or a specific wavelength may be used in the present invention. Examples of those are BHQ and DABCYL.

In the FRET label adopted to the CTO, the reporter encompasses a donor of FRET and the quencher encompasses the other partner (acceptor) of FRET. For example, a fluorescein dye is used as the reporter and a rhodamine dye as the quencher.

The labels may be linked to the CTO or PTO-NV by conventional methods. Particularly, it is linked to the CTO or PTO-NV through a spacer containing carbon atoms (e.g., 3-carbon spacer, 6-carbon spacer or 12-carbon spacer).

(i-2) Single Label

The present invention is also excellently executed using single label systems for providing signals indicating the presence of target nucleic acid sequences.

According to an embodiment, the first fragment or the CTO has a single label, and the melting of the extended duplex in the step (e) induces change of a signal from the single label to give the target signal in the step (e).

First Embodiment Single Label System

The templating portion of the CTO may have a single fluorescent label. The PTO-NV hybridized with the target nucleic acid sequence is digested to release the first fragment. The first fragment is hybridized with the capturing portion of the CTO and extended to form the extended duplex. By the formation of the extended duplex, the fluorescent intensity from the single fluorescent label becomes increased. When the extended duplex is melted in the step (e), the fluorescent intensity from the single fluorescent label becomes decreased, such that the target signal is given to indicate the presence of the extended stand in the step (e).

According to an embodiment, the single label may be located at any site on the CTO, so long as the signal level from the single label is changed depending on melting of the extended duplex.

According to an embodiment, the single label is linked to the templating portion or to the capturing portion of the CTO.

Where the templating portion of the CTO is labeled with a single label, a signal change from the label on the hybrid between the uncleaved PTO-NV and the CTO is not induced. Therefore, the hybrid does not provide a non-target signal.

Where the capturing portion of the CTO is labeled with a single label, the hybrid between the uncleaved PTO-NV and the CTO provides a non-target signal in the melting step. In this case, the difference in $T_m$ values of the extended duplex and the hybrid permits to discriminate the target signal of the extended duplex from the non-target signal of the hybrid.

Second Embodiment Single Label System

The 5'-tagging portion of the PTO-NV may have a single fluorescent label. The PTO-NV hybridized with the target nucleic acid sequence is digested to release the first fragment comprising the 5'-tagging portion with the single fluorescent label. By the hybridization, the signal intensity from the single fluorescent label on the 5'-tagging portion is increased. When the extended duplex is melted in the step (e), the signal intensity from the single fluorescent label becomes decreased, such that the target signal is given to indicate the presence of the extended strand in the step (e).

According to an embodiment, the single label may be located at any site on the first fragment, so long as the signal level from the single label is changed depending on melting of the extended duplex.

The hybrid between the uncleaved PTO-NV and the CTO may provide a non-target signal in the melting step. In this case, the difference in $T_m$ values of the extended duplex and the hybrid permits to discriminate the target signal of the extended duplex from the non-target signal of the hybrid.

The single label used herein has to be capable of providing a different signal depending on its presence on a double strand or single strand. The single label includes a fluorescent label, a luminescent label, a chemiluminescent label, an electrochemical label and a metal label. Preferably, the single label includes a fluorescent label.

The types and preferable binding sites of single fluorescent labels used in this invention are disclosed U.S. Pat. Nos. 7,537,886 and 7,348,141, the teachings of which are incorporated herein by reference in their entity. Preferably, the single fluorescent label includes JOE, FAM, TAMRA, ROX and fluorescein-based label. The labeled nucleotide residue is preferably positioned at internal nucleotide residue within the oligonucleotide rather than at the 5'-end or the 3'-end.

The single fluorescent label useful in the present invention may be described with reference to descriptions for reporter and quencher molecules as indicated above.

In particular, where the present invention on a solid phase is performed using a single label, it can utilize a general fluorescent label and does not require a specific fluorescent label capable of providing a fluorescent signal with different intensities depending on its presence on double strand or single strand. The target signal provided on the solid substrate is measured.

When the CTO immobilized onto a solid substrate is used, chemical labels (e.g. biotin) or enzymatic labels (e.g. alkaline phosphatase, peroxidase, β-galactosidase and β-gluocosidase) may be used.

In the labeling system using "label linked to the first fragment and/or the CTO", the labels may be positioned to the extent that when a hybrid between an uncleaved PTO-NV and the CTO is formed, the hybrid does not give a non-target signal in the step (e). Alternatively, the labels may be positioned to the extent that when a hybrid between an uncleaved PTO-NV and the CTO is formed, the hybrid gives a non-target signal in the step (e); wherein the $T_m$ value of the extended duplex is higher than that of the hybrid between the uncleaved PTO-NV and the CTO.

Particularly, where the labels are positioned to the extent that a hybrid between an uncleaved PTO-NV and the CTO does not give a non-target signal, the range including $T_m$ value of the hybrid can be utilized to select $T_m$ value of the extended duplex for detecting a target nucleic acid sequence.

(ii) Label Incorporated into the Extended Duplex

The present invention may employ a label incorporated into the extended duplex during the extension reaction for providing the target signal indicative of the presence of the extended strand.

Although the first fragment or CTO has no label, a label incorporated into the extended duplex during the extension reaction is successfully used to allow the extended duplex to be labeled.

According to an embodiment, the target signal is provided by a single label incorporated into the extended duplex during the extension reaction; wherein the incorporated single label is linked to a nucleotide incorporated during the extension reaction; wherein the melting of the extended duplex in the step (e) induces change of a signal from the single label to give the target signal in the step (e).

For example, the PTO-NV hybridized with the target nucleic acid sequence is digested to release the first fragment. The first fragment is hybridized with the capturing portion of the CTO immobilized on a solid substrate and extended in the presence of nucleotides labeled with the single fluorescent label to form the extended duplex. The fluorescent signal from the extended duplex may be detected on spot of the solid substrate with immobilized CTO. When the extended duplex is melted, a strand having a fluorescent label is released and the fluorescent signal is no longer detected on the spot. Therefore, a signal change can be provided on the spot by melting of the extended duplex. In this regard, the target signal is given to indicate the presence of the extended strand in the step (e).

The target signal given in the step (e) includes a melting curve, a melting pattern or a $T_m$ value that is obtained by measuring change of the fluorescent intensity on the CTO-immobilized spot.

According to an embodiment, a nucleotide incorporated during the extension reaction is a ddNTP.

According to an embodiment, a nucleotide incorporated during the extension reaction has a first non-natural base and the CTO has a nucleotide having a second non-natural base with a specific binding affinity to the first non-natural base. The nucleotide having the second non-natural base is preferably located at any site on the templating portion of the CTO.

The term used herein "non-natural base" refers to derivatives of natural bases such as adenine (A), guanine (G), thymine (T), cytosine (C) and uracil (U), which are capable of forming hydrogen-bonding base pairs. The term used herein "non-natural base" includes bases having different base pairing patterns from natural bases as mother compounds, as described, for example, in U.S. Pat. Nos. 5,432,272, 5,965,364, 6,001,983, and 6,037,120. The base pairing between non-natural bases involves two or three hydrogen bonds as natural bases. The base pairing between non-natural bases is also formed in a specific manner.

Specific examples of non-natural bases include the following bases in base pair combinations: iso-C/iso-G, iso-dC/iso-dG, K/X, H/J, and M/N (see U.S. Pat. No. 7,422,850).

For example, the first fragment is hybridized with the CTO with a nucleotide having a second non-natural base (e.g., iso-dC) with a specific binding affinity to a first non-natural base (e.g., iso-dG). The extension is carried out in the presence of a nucleotide having the first non-natural base labeled with a single fluorescent label, forming the extended duplex. In the extension reaction, the nucleotide having the first non-natural base is incorporated at an opposition site to the nucleotide having the second non-natural base.

The fluorescent signal from the extended duplex may be detected on spot of a solid substrate with immobilized CTO. When the extended duplex is melted, a strand having a fluorescent label is released and the fluorescent signal is no longer detected on the spot. Therefore, a signal change can be provided on the spot by melting of the extended duplex. In this regard, the target signal is given to indicate the presence of the extended strand in the step (e).

Where the label incorporated into the extended duplex during the extension reaction is employed, the label is not incorporated into the hybrid between the uncleaved PTO-NV and the CTO because the hybrid is not extended. Therefore, the hybrid does not provide a non-target signal.

The types and characteristics of the single labels used may be described with reference to descriptions for the labeling system using "label linked to the first fragment and/or the CTO" as indicated hereinabove.

(iii) Label Incorporated into the Extended Duplex and Label Linked to the First Fragment or the CTO The present invention may employ a labeling system using cooperation of a label incorporated into the extended duplex during the extension reaction and a label linked to the first fragment and/or the CTO.

According to an embodiment, the target signal is provided by a label incorporated into the extended duplex during the extension reaction and a label linked to the first fragment and/or the CTO, and the incorporated label is linked to a nucleotide incorporated during the extension reaction; wherein the two labels are an interactive dual label of a reporter molecule and a quencher molecule; wherein the melting of the extended duplex in the step (e) induces change of a signal from the interactive dual label to give the target signal in the step (e).

Particularly, the nucleotide incorporated during the extension reaction has a first non-natural base and the CTO has a nucleotide having a second non-natural base with a specific binding affinity to the first non-natural.

For example, the first fragment is hybridized with the CTO comprising a reporter or quencher molecule and a nucleotide having a second non-natural base (e.g., iso-dC) which is a specific binding affinity to a first non-natural base (e.g., iso-dG). The extension is carried out in the presence of a nucleotide having the first non-natural base labeled with a quencher or reporter molecule, forming the extended duplex in which the signal from the reporter molecule is quenched by the quencher molecule. In the extension reaction, the nucleotide having the first non-natural base is incorporated at an opposition site to the nucleotide having the second non-natural base.

When the extended duplex is melted in the step (e), the reporter molecule and the quencher molecule are separated to allow the quencher molecule to unquench the signal from the reporter molecule, such that the target signal is given to indicate the presence of the extended strand in the step (e).

Particularly, the target signal given in the step (e) includes a melting curve, a melting pattern or a $T_m$ value that is obtained by measuring change of the signal from the interactive dual label.

The site of the label on the CTO and the incorporation site of the label incorporated are determined to the extent that the two labels are acted as an interactive dual label for inducing signal change in the melting step.

Particularly, the templating portion of the CTO has a reporter or quencher molecule and a nucleotide having a second non-natural base. The extension reaction in the step (d) is performed in the presence of a nucleotide having a quencher or reporter molecule and a first non-natural base with a specific binding affinity to the second non-natural base in the CTO. The two non-natural bases in the extended duplex in the step (d) form a base-pairing to quench a signal from the reporter molecule by the quencher molecule and to induce change of a signal, whereby the target signal is provided. Alternatively, the first fragment has a reporter or quencher molecule and the templating portion of the CTO has a nucleotide having a second non-natural base. The extension reaction in the step (d) is performed in the presence of a nucleotide having a quencher or reporter molecule and a first non-natural base with a specific binding affinity to the second non-natural base in the CTO. The two non-natural bases in the extended duplex in the step (d) form a base-pairing to induce change a signal from the reporter molecule by quenching, whereby the target signal is provided.

As another example, the first fragment having a reporter or quencher molecule is hybridized with the CTO comprising a nucleotide having a second non-natural base (e.g., iso-dC) which is a specific binding affinity to a first non-natural base (e.g., iso-dG). The extension is carried out in the presence of a nucleotide having the first non-natural base labeled with a quencher or reporter molecule, forming the extended duplex in which the signal from the reporter molecule is quenched by the quencher molecule. In the extension reaction, the nucleotide having the first non-natural base is incorporated at an opposition site to the nucleotide having the second non-natural base.

When the extended duplex is formed in the step (d), the reporter molecule and the quencher molecule are conformationally separated to allow the quencher molecule to unquench the signal from the reporter molecule; wherein when the extended duplex is melted in the step (e), the reporter molecule and the quencher molecule are conformationally adjacent to each other to allow the quencher molecule to quench the signal from the reporter molecule, such that the target signal is given to indicate the presence of the extended strand in the step (e).

Particularly, the target signal given in the step (e) includes a melting curve, a melting pattern or a $T_m$ value that is obtained by measuring change of the signal from the interactive dual label.

The site of the label on the PTO-NV and the incorporation site of the label incorporated are determined to the extent that the two labels are acted as an interactive dual label for inducing signal change in the melting step.

Where the label incorporated into the extended duplex during the extension reaction is employed, the label is not incorporated into the hybrid between the uncleaved PTO-NV and the CTO because the hybrid is not extended. Therefore, the hybrid does not provide a non-target signal in the melting step.

(iv) Intercalating Label

The present invention may employ an intercalating label for providing the target signal indicative of the presence of the extended duplex. The intercalating label is more useful on a solid phase reaction using immobilized CTOs because double-stranded nucleic acid molecules present in samples can generate signals.

Exemplified intercalating dyes useful in this invention include SYBR™ Green I, PO-PRO™-1, BO-PRO™-1, SYTO™43, SYTO™44, SYTO™45, SYTOX™Blue, POPO™-1, POPO™-3, BOBO™-1, BOBO™-3, LO-PRO™-1, JO-PRO™-1, YO-PRO™1, TO-PRO™1, SYTO™11, SYTO™13, SYTO™15, SYTO™16, SYTO™20, SYTO™23, TOTO™-3, YOYO™3, GelStar™ and thiazole orange. The intercalating dyes intercalate specifically into double-stranded nucleic acid molecules to generate signals.

In certain embodiment, the first fragment is hybridized with the capturing portion of the CTO immobilized on a solid substrate. The extension is carried out in the presence of an intercalating dye (e.g., SYBR™ Green) and produces the extended duplex with intercalating dyes. The fluorescent signal from the extended duplex on spot of the solid substrate with immobilized CTO may be detected using intercalating fluorescent dyes. When the extended duplex is melted, intercalating fluorescent dyes are released and the fluorescent signal is no longer detected on the spot. In this regard, the target signal is given to indicate the presence of the extended duplex in the step (e).

The hybrid between the uncleaved PTO-NV and the CTO provides a non-target signal in the melting step. In this case, the difference in $T_m$ values of the extended duplex and the hybrid permits to discriminate the target signal of the extended duplex from the non-target signal of the hybrid.

Particularly, the target signal given in the step (e) includes a melting curve, a melting pattern or a $T_m$ value that is obtained by measuring change of the fluorescent signal generated in the step (d).

Detection of Extended Duplex at Predetermined Temperature

According to an embodiment, the detection in the step (e) is carried out in accordance with the PTOCE assay comprising detection at a pre-determined temperature using signals from the extended duplex between the extended strand and the CTO (see WO 2012/096523).

According to an embodiment, the extended strand of the first fragment and the CTO form an extended duplex in the step (d); wherein the extended duplex has a $T_m$ value adjustable by (i) a sequence and/or length of the first fragment, (ii) a sequence and/or length of the CTO or (iii) the sequence and/or length of the first fragment and the sequence and/or length of the CTO; wherein the extended duplex provides a target signal by (i) at least one label linked to the first fragment and/or CTO, (ii) a label incorporated into the extended duplex during the extension reaction, (iii) at least one label linked to the first fragment and/or CTO and a label incorporated into the extended duplex during the extension reaction or (iv) intercalating label; and wherein the presence of the extended strand is detected by measuring the target signal from the extended duplex at a pre-determined temperature sufficient to maintain a double strand of the extended duplex.

The extended duplex per se can give signal capable of discriminating formation from no-formation of the extended duplex and the signal is detected at a predetermined temperature that the extended duplex maintains its double-stranded form, whereby the presence of a target nucleic acid sequence is determined.

The present invention is to measure a target signal in association with the formation of the extended duplex, for detection of the presence of the target nucleic acid sequence.

In the present invention, the extended duplex has a label such that the extended duplex provides a target signal.

The label system used for detection of the extended duplex by melting or hybridization analysis can provide the target signal in the present method.

The working principle underlying a target signal from the extended duplex is as follows: (i) the extension of the first fragment induces change of a signal from a label to give the target signal; or (ii) the hybridization of the first fragment and the CTO induces change of a signal from a label to give the target signal and the extended duplex maintains the target signal.

For example, where immobilized CTOs are used, the present invention detects a plurality of target nucleic acid sequences in much more effective manner. The templating portion of the immobilized CTO has a reporter molecule and a quencher molecule. The reporter molecule and the quencher molecule are conformationally adjacent to each other to allow the quencher molecule to quench a signal from the reporter molecule. When the first fragment is hybridized with the capturing portion of the CTO, the quencher molecule quenches the signal from the reporter molecule. By the formation of the extended duplex, the reporter molecule and the quencher molecule are conformationally separated to allow the quencher molecule to unquench the signal from the reporter molecule. The target signal is given in the extension step.

In certain embodiment, the 5'-tagging portion of the PTO-NV has a reporter molecule and a quencher molecule. The reporter molecule and the quencher molecule are conformationally adjacent to each other to allow the quencher molecule to quench a signal from the reporter molecule. The PTO-NV hybridized with the target nucleic acid sequence is digested to release the first fragment comprising the 5'-tagging portion with the reporter molecule and the quencher molecule, and the first fragment is hybridized with the capturing portion of the CTO. By the hybridization, the reporter molecule and the quencher molecule are conformationally separated to allow the quencher molecule to unquench the signal from the reporter molecule. The target signal is given in the fragment hybridization step and the extended duplex maintains the target signal.

In such case that the 5'-tagging portion of the PTO-NV has a reporter molecule and a quencher molecule, the hybrid between the uncleaved PTO and the CTO provides non-target signal and it is necessary to dissociate the hybrid to remove the non-target signal. Therefore, the temperature for measuring the target signal is determined to dissociate the hybrid. According to an embodiment, the temperature is further determined in consideration of hybrid's $T_m$ value.

According to an embodiment, the extended duplex may be detected at temperatures that the hybrid is partially dissociated. According to an embodiment, the extended duplex may be detected at temperatures that the hybrid is sufficiently dissociated to remove the non-target signal.

According to an embodiment, the predetermined temperature is higher than the hybrid's $T_m$ value minus 10° C., preferably, higher than the hybrid's $T_m$ value minus 5° C., more preferably, higher than the hybrid's $T_m$ value and still more preferably, higher than the hybrid's $T_m$ value plus 5° C.

Detection Using Signaling Oligonucleotide

According to an embodiment, the extended strand of the first fragment may be detected by using a signaling oligonucleotide (SO) as disclosed in PCT/KR2012/005281.

The SO to be hybridized with the extended strand comprises a complementary sequence to the extended strand. According to an embodiment, the SO comprises a complementary sequence to the extended sequence.

According to an embodiment, at least a portion of the SO comprises a complementary sequence to the extended sequence. The portion of the SO comprising a complementary sequence to the extended sequence is at least one, two, three, four, five or ten nucleotides in length.

When a portion of the SO is designed to comprise a complementary sequence to a portion of the extended sequence newly synthesized, the $T_m$ value of the hybridization resultant of the SO and the extended strand becomes different from that of the hybridization resultant of the SO and the undigested PTO-NV. The difference in the $T_m$ values ensures to differentiate signals from the two hybridization resultants. For example, non-target signals may be excluded in a real-time detection by adjusting temperature for detection in considering $T_m$ values, or in a melting curve analysis by melting peaks.

The SO may comprise throughout its whole sequence a complementary sequence to the extended sequence. Alternatively, the SO may comprise a portion having a complementary sequence to the extended sequence. For instance, one portion of the SO may comprise a complementary sequence to the extended sequence and the other portion may comprise a complementary sequence to the fragment. Particularly, the SO comprises throughout its whole sequence a complementary sequence to the extended sequence.

The SO may have any length, for example, 5-100 nucleotides, 5-80 nucleotides, 5-60 nucleotides, 5-40 nucleotides, 5-20 nucleotides, 5-10 nucleotides, 10-100 nucleotides, 10-80 nucleotides, 10-60 nucleotides, 10-40 nucleotides, 10-30 nucleotides, 10-20 nucleotides, 15-100 nucleotides, 15-80 nucleotides, 15-60 nucleotides, 15-40 nucleotides, 15-30 nucleotides, 15-20 nucleotides, 20-100 nucleotides, 20-80 nucleotides, 20-60 nucleotides, 20-40 nucleotides or 20-30 nucleotides.

The SO may have a hairpin structure.

The 3'-end of the SO is blocked to prohibit its extension. Alternatively, the SO having a non-blocked 3'-OH end may be extended.

According to an embodiment, wherein the extended strand of the first fragment is detected by using a signaling oligonucleotide (SO); wherein the SO comprises a complementary sequence to the extended strand and at least one label; the SO provides a detectable signal by association with or dissociation from the extended strand.

The term "association with or dissociation from the extended strand" has the same meaning as the term "hybridization with or denaturation from the extended strand".

According to an embodiment, the detectable signal indicative of the presence of the target nucleic acid sequence is provided by (i) the label linked to the SO, (ii) a combination of the label linked to the SO and a label linked to the fragment from the PTO-NV, (iii) a combination of the label linked to the SO and a label to be incorporated into the extended strand during the extension reaction of the step (d), or (iv) a combination of the label linked to the SO and an intercalating dye.

Briefly, the labeling systems useful in this invention will be described as follows:

(i) Single Label Linked to the SO

The present invention may provide signal for formation of the extended strand indicating the presence of the target nucleotide variation by using SO with a single label. According to an embodiment, the SO is labeled with a single label and the hybridization between the SO and the extended strand in the step (e) induces change in signal from the single label to provide the detectable signal.

In an embodiment, the single label used herein has to be capable of providing a different signal depending on its presence on a double strand or single strand.

(ii) Intrastrand Interactive-Dual Label Linked to SO

Figure 6:
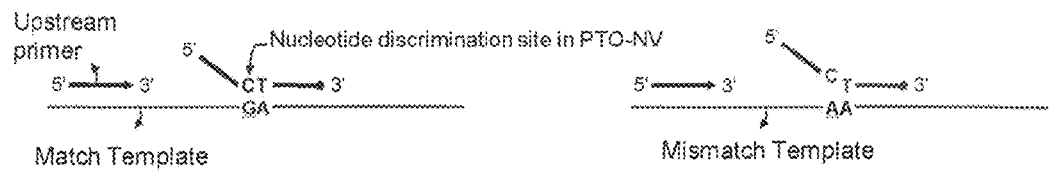
FIG. 6 schematically represents the selective detection of a target nucleotide variation by the AB-VD PTOCE of the present invention using the SO (signaling oligonucleotide).
Figure 6:
Figure 6:
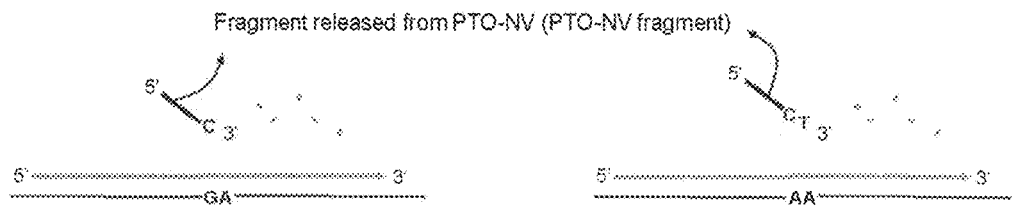
Figure 6:
Figure 6:
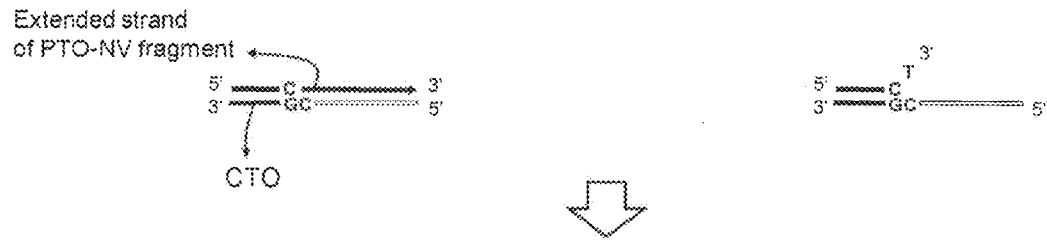
Figure 6:
Figure 6:
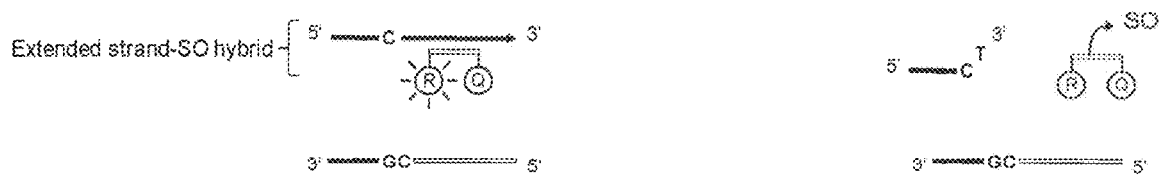
Figure 6:

According to an embodiment, the SO is labeled with an interactive dual label comprising a reporter molecule and a quencher molecule and the hybridization between the SO and the extended strand in the step (e) induces change in signal from the interactive dual label to provide the detectable signal (see FIG. 6). Prior to hybridization of the SO, the reporter molecule and the quencher molecule on the SO are conformationally adjacent to each other to allow the quencher molecule to quench the signal from the reporter molecule. Upon hybridization, the reporter molecule and the quencher molecule on the SO are conformationally separated to allow the quencher molecule to unquench the signal from the reporter molecule, causing changes in signals from the interactive dual label.

According to an embodiment of the present invention using the SO with an interactive dual label, the first fragment released from the PTO-NV hybridized with the target nucleic acid sequence is hybridized with the capturing portion of the CTO and extended to form the extended strand. Upon hybridization of the extended strand with the SO, the reporter molecule and the quencher molecule on the SO are conformationally separated to allow the quencher molecule to unquench the signal from the reporter molecule, giving rise to changes in signals from the interactive dual label (e.g., increase in signal from reporter molecules). The reporter molecule and the quencher molecule on the SO not involved in the hybridization are conformationally adjacent to each other to allow the quencher molecule to quench the signal from the reporter molecule.

According to an embodiment, the reporter molecule and the quencher molecule are positioned at the 5'-end (or 3'-end) and 3'-end (or 5'-end) of the SO. According to an embodiment, one of the reporter molecule and the quencher molecule on the SO is located at its 5'-end or at 1-5 nucleotides apart from its 5'-end and the other is located to quench and unquench the signal from the reporter molecule depending on conformation of the SO.

According to an embodiment, one of the reporter molecule and the quencher molecule on the SO is located at its 3'-end or at 1-5 nucleotides apart from its 3'-end and the other is located to quench and unquench the signal from the reporter molecule depending on conformation of the SO.

(iii) Interstrand Interactive-Dual Label

In the embodiment using the interstrand interactive-dual label, the extended strand has one of an interactive dual label comprising a reporter molecule and a quencher molecule and the SO has the other of the interactive dual label.

The embodiment using the interstrand interactive-dual label may be conducted in accordance with the following three fashions:

According to the first fashion, the SO comprises one label among a reporter molecule and a quencher molecule of an interactive dual label, the fragment from the PTO-NV comprises the other label among the reporter molecule and the quencher molecule; the extended strand comprises the label originated from the fragment from the PTO-NV, and wherein the hybridization between the SO and the extended strand induces change in signal from the interactive dual label to provide the detectable signal.

A label linked to the SO may be either a reporter molecule or a quencher molecule, and a label to the fragment may be either a quencher molecule or a reporter molecule.

The labeling site on the PTO-NV is determined in considering its cleavage site, so that the PTO-NV fragment may have the label.

The label may be linked to any site (e.g., the tagging portion of the PTO-NV) on the PTO-NV fragment, so long as it interacts with the label to the SO upon hybridization with the SO to induce change in signals. The label may be linked to any site (e.g., the 5'-end of the SO) on the SO, so long as it interacts with the label on the PTO-NV fragment upon hybridization with the PTO-NV fragment to induce change in signals.

According to the second fashion, the SO comprises one label among a reporter molecule and a quencher molecule of an interactive dual label, and the templating portion of the CTO comprises a nucleotide having a first non-natural base; wherein the extension reaction in the step (d) is performed in the presence of a nucleotide having both a second non-natural base with a specific binding affinity to the first non-natural base and the other among the reporter molecule and the quencher molecule, thereby incorporating the label into the extended strand; wherein the hybridization between the SO and the extended strand induces change in signal from the interactive dual label to provide the detectable signal.

The label incorporated during the extension is preferably linked to a nucleotide, more preferably to a nucleoside triphosphate. Preferably, the label is bound to a base of a nucleoside triphosphate.

The fragment is hybridized with the CTO with a nucleotide having a non-natural base (e.g., iso-dC) with a specific binding affinity to a non-natural base (e.g., iso-dG). The extension is carried out in the presence of a nucleotide having the iso-dG labeled with a quencher to form the extended strand. In the extension reaction, the nucleotide having iso-dG with a quencher is incorporated at an opposition site to the nucleotide having iso-dC. Following the hybridization of the extended strand containing the quencher-iso-dG with the SO labeled with a reporter, the quencher on the extended strand quenches signal from the reporter on the SO to induce changes in signal, providing the detectable signal.

One of the interactive dual label is linked to the SO and the other is incorporated into the extended strand from a reaction solution during the extension reaction.

A label linked to the SO may be either a reporter molecule or a quencher molecule, and a label incorporated into the extended strand may be either a quencher molecule or a reporter molecule.

The label incorporated into the extended strand may be linked to any site on the extended strand (e.g., the 3'-end of the extended strand), so long as it interacts with the label to the SO upon hybridization with the SO to induce change in signals.

The label may be linked to any site (e.g., the 5'-end of the SO) on the SO, so long as it interacts with the label incorporated into the extended strand upon hybridization with the extended strand to induce change in signals.

According to the third fashion, the SO comprises one label among a reporter molecule and a quencher molecule of an interactive dual label, and the extension reaction in the step (d) is performed in the presence of a nucleotide having the other among the reporter molecule and the quencher molecule, thereby incorporating the label into the extended strand; wherein the hybridization between the SO and the extended strand induces change in signal from the interactive dual label to provide the detectable signal.

A label linked to the SO may be either a reporter molecule or a quencher molecule (preferably reporter molecule), and a label incorporated into the extended strand may be either a quencher molecule or a reporter molecule (preferably quencher molecule).

(iv) Interactive-Dual Label Using Two SOs

In the embodiment of the interactive-dual label using two SOs, the method of the present invention uses an additional SO comprising a complementary sequence to the extended strand, the two SOs are hybridized with the extended strand in an adjacent manner, the two SOs each comprises one label among a reporter molecule and a quencher molecule of an interactive dual label; and the hybridization between the two SOs and the extended strand induces change in signal from the interactive dual label to provide the detectable signal.

Particularly, at least one of the two SOs comprises a portion hybridized to a newly extended sequence in the extension reaction.

The principle underlying the performance of the embodiment of the interactive-dual label using two SOs are as follows: The first fragment released from the PTO-NV hybridized with the target nucleic acid sequence having the target nucleotide variation is hybridized with the capturing portion of the CTO and extended to form the extended strand. Afterwards, the two SOs are hybridized with the extended strand. In the hybridization, since the two SOs are adjacently hybridized with the extended strand, the reporter molecule and the quencher molecule on the two SOs are adjacent to each other to allow the quencher molecule to quench the signal from the reporter molecule, resulting in change in signals from the interactive dual label (e.g., increase in signal from reporter molecules). The reporter molecule and the quencher molecule on the two SOs not involved in the hybridization are separated to each other to generate signal from the reporter molecule.

According to an embodiment, the two SOs may be hybridized with any sites of the extended strand so long as their hybridization with the extended strand permits the quencher molecule to quench the signal from the reporter molecule. Preferably, the two SOs are positioned in an immediately adjacent manner or 1-5 nucleotides apart from each other.

According to an embodiment, where the two SOs may be adjacently hybridized with the extended strand, the reporter molecule and the quencher molecule may be linked to any sites of the two SOs so long as the quencher molecule quenches the signal from the reporter molecule. For example, the reporter molecule or the quencher molecule is linked to the 5'-end of one SO or 1-5 nucleotides apart from its 5'-end, and the quencher molecule or the reporter molecule to the 3'-end of the other SO or 1-5 nucleotides apart from its 3'-end.

(v) FRET Label Using Intercalating Dyes

According to the present invention, a FRET (fluorescence resonance energy transfer) signaling becomes practical using intercalating dyes.

According to an embodiment, the SO comprises an acceptor of a FRET and the hybridization in the step (e) is preformed in the presence of an intercalating dye; wherein the hybridization between the SO and the extended strand induces change in signal from the acceptor of the SO to provide the detectable signal.

The principle underlying the performance of the embodiment of the FRET label using intercalating dyes are as follows: The first fragment released from the PTO-NV hybridized with the target nucleic acid sequence having the target nucleotide variation is hybridized with the capturing portion of the CTO and extended to form the extended strand. Afterwards, the SO labeled with the acceptor is hybridized with the extended strand to form a double-stranded nucleic acid molecule and then the intercalating dyes are bound to the double-stranded nucleic acid molecule. The energy transfer occurs from the intercalating dyes serving as a donor molecule to the acceptor by illumination for donor excitation and induces change in signal from the acceptor to provide the detectable signal.

According to an embodiment, the acceptor linked to the SO includes various single fluorescent labels described above, but not limited to.

The SO useful in the present invention includes any probes capable of providing signals dependent on hybridization, for example, Molecular beacon™ (U.S. Pat. No. 5,925,517), Hybeacons™ (D. J. French, et al., Molecular and Cellular Probes (2001) 13, 363-374 and U.S. Pat. No. 7,348,141), Dual-labeled, self-quenched probe (U.S. Pat. No. 5,876,930), LUX™ (I. A. Nazarenko, et al. Nucleic Acids Res 2002, 30:2089-2095. and U.S. Pat. No. 7,537, 886) and Hybridization probe (Bernard P S, et al., Clin Chem 2000, 46, 147-148 and Deepti Parashar et al., Indian J Med Res 124, review article October 2006 385-398).

According to an embodiment, detection using SO may be carried out in a real-time manner using labels proving signals detectable in a real-time fashion.

Alternatively, the detection using SO may be carried out by a melting analysis or hybridization analysis because the labels used in the present invention are capable of providing detectable signals during melting of the hybridization resultant or melting and hybridization of the hybridization resultant.

According to an embodiment, the extended strand may be further amplified by using a primer forming a pair of primers with the PTO-NV fragment.

According to an embodiment, the SO is blocked at its 3'-end to prohibit its extension.

Detection Using Hybridizing Oligonucleotide

According to an embodiment, the extended strand of the first fragment is detected by using a HO (hybridizing oligonucleotide); wherein the HO comprises a hybridizing nucleotide sequence complementary to the CTO and at least one label; wherein the extension of the first fragment induces the cleavage of the HO by an enzyme having a 5' nuclease activity to generate a detectable signal from the label.

According to an embodiment, the HO is located downstream of the first fragment on the CTO.

According to an embodiment, the HO comprises a hybridizing nucleotide sequence complementary to the templating portion of the CTO.

According to an embodiment, the template-dependent nucleic acid polymerase used for the extension of the fragment has a 5' nuclease activity.

The length of the HO may be widely varied. For example, the HO is 5-100 nucleotides, 5-80 nucleotides, 5-60 nucleotides, 5-40 nucleotides, 5-20 nucleotides, 5-10 nucleotides, 10-100 nucleotides, 10-80 nucleotides, 10-60 nucleotides, 10-40 nucleotides, 10-30 nucleotides, 10-20 nucleotides, 15-100 nucleotides, 15-80 nucleotides, 15-60 nucleotides, 15-40 nucleotides, 15-30 nucleotides, 15-20 nucleotides, 20-100 nucleotides, 20-80 nucleotides, 20-60 nucleotides, 20-40 nucleotides or 20-30 nucleotides in length.

In an embodiment of this invention, the HO is blocked at its 3'-end to prohibit its extension.

Briefly, the labeling systems useful in this invention will be described as follows:

(i) Single Label Linked to the HO

The present invention may provide signal for formation of the extended strand indicating the presence of the target nucleotide variation by using HO with a single label.

In an embodiment, the single label used herein has to be capable of providing a different signal depending on its presence on a double strand or single strand (e.g. the HO and the fragment of HO).

According to an embodiment, it is necessary to detect signal at temperature to allow for hybridization between the HO and the CTO.

(ii) Interactive Dual Label Linked to the HO

According to an embodiment, the detectable signal is provided by an interactive dual label linked to the HO.

Figure 7:
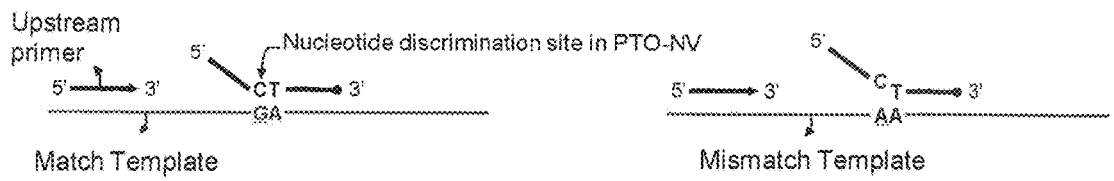
FIG. 7 schematically represents the selective detection of a target nucleotide variation by the AB-VD PTOCE of the present invention using the HO (hybridizing oligonucleotide).
Figure 7:
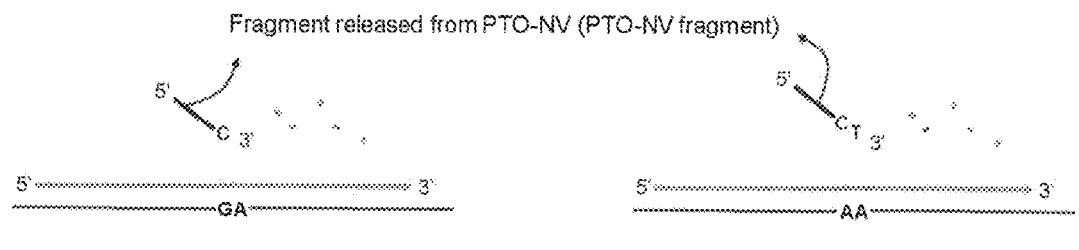
Figure 7:
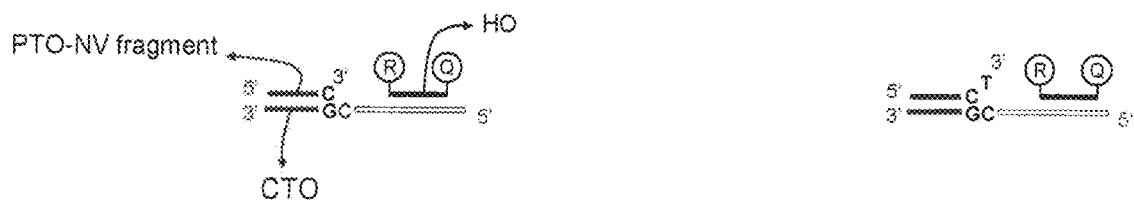
Figure 7:

As illustrated in FIG. 7, the first fragment released from the PTO-NV is hybridized with the capturing portion of the CTO and the HO labeled with an interactive dual label comprising a reporter molecule and a quencher molecule is hybridized with the templating portion of the CTO. The extension of the first fragment induces cleavage of the HO to separate the reporter molecule from the quencher molecule, thereby providing a signal indicating the presence of the extended strand.

In such embodiment, where the dual label-linked nucleotides are relatively adjacent to each other, signal changes between before and after the HO cleavage may be utilized for signal detection.

Where the dual label-linked nucleotides are relatively distal to each other, the hybridization between the HO and the CTO induces conformational separation of the interactive dual label to unquench the signal from the reporter molecule even with no HO cleavage, thereby generating a signal change. In this case, the signal from a cleaved fragment of the HO may be detected at higher temperatures (e.g., 95° C.) to allow for prevention of hybridization between the HO and the CTO.

According to an embodiment, the reporter molecule and the quencher molecule may be located at any site on the HO, so long as the cleaved HO and the uncleaved HO can provide discriminative signals.

In certain embodiment, the reporter molecule and the quencher molecule each is located at both ends of the HO.

(iii) Interactive Dual Label Linked to the HO and the CTO

According to an embodiment, the detectable signal is provided by one of an interactive dual label comprising a reporter molecule and a quencher molecule linked to the HO and the other linked to the CTO.

In certain embodiment, the reporter molecule and the quencher molecule are positioned on the HO and the CTO such that a signal from the reporter molecule is quenched by the quencher molecule when the HO is hybridized to CTO. The cleavage of the HO induced by extension of the first fragment allows to release the HO from the CTO and separate the reporter molecule from the quencher molecule and then the quencher molecule to unquench the signal from the reporter molecule, thereby providing a signal indicating the presence of the extended strand.

According to an embodiment, it is necessary to detect signal at temperatures to allow for hybridization between the HO and the CTO.

In an embodiment, the HO may be designed to have a hairpin structure.

In certain embodiment, one of the reporter molecule and the quencher molecule is linked to the 3'-end of the HO and the other is linked to the 5'-end of the CTO.

According to an embodiment, the label system such as interactive-dual label using two HOs may be employed in the present method using HO. The interactive-dual label may be located at any site on the two HOs, so long as the cleaved HO and the uncleaved HO can provide discriminative signals. The types and locations of labels may be described with reference to descriptions for the SO.

According to an embodiment, the label system such as FRET label using intercalating dyes may be employed in the present method using HO. The FRET label may be located at any site on the HO, so long as the cleaved HO and the uncleaved HO can provide discriminative signals in the presence of the intercalating dye. The types and locations of labels may be described with reference to descriptions for the SO.

Detection by Size or Sequence of Extended Strand

According to an embodiment, the extended strand of the first fragment may be detected on the basis of either the size or sequence of the extended strand. For example, the extended strand can be detected by using an electrophoresis or a mass analysis (e.g., electron impact (EI), chemical ionization (CI), Field Desoption (FD), 252Cf-Plasma desoprtion (PD), desoprtion chemical ionization (DCI), secondary ion mass spectrometry (SIMS), fast atom bombardment (FAB), electrospray ionization (ESI), matrix-assisted laser desoprtion ionization (MALDI) and Tandem Mass Spectrometry).

The PTO-NV and CTO may be comprised of naturally occurring dNMPs. Alternatively, the PTO-NV and CTO may be comprised of modified nucleotide or non-natural nucleotide such as PNA (peptide nucleic acid, see PCT Publication No. WO 92/20702) and LNA (locked nucleic acid, see PCT Publication Nos. WO 98/22489, WO 98/39352 and WO 99/14226). The PTO-NV and CTO may comprise universal bases such as deoxyinosine, inosine, 1-(2'-deoxy-beta-D-ribofuranosyl)-3-nitropyrrole and 5-nitroindole. The term "universal base" refers to one capable of forming base pairs with each of the natural DNA/RNA bases with little discrimination between them.

According to an embodiment, the method further comprises repeating all or some of the steps (a)-(e) with denaturation between repeating cycles. The reaction repetition is accompanied with amplification of the target nucleic acid sequence. Preferably, the amplification is performed in accordance with PCR (polymerase chain reaction) which is disclosed in U.S. Pat. Nos. 4,683,195, 4,683,202, and 4,800,159.

According to an embodiment, the method further comprises repeating the steps (a)-(b), (a)-(d) or (a)-(e) with denaturation between repeating cycles. For example, the method may be carried out by repeating the steps (a)-(b), (a)-(d) or (a)-(e) for several cycles, e.g., 2-80 cycles, 2-50 cycles, 2-40 cycles, 10-80 cycles, 10-50 cycles, 10-40 cycles, 20-80 cycles, 20-50 cycles, 20-40 cycles, 30-60 cycles or 40-60 cycles with denaturation between repeating cycles, and then performing the step (e). For example, the method may be also carried out by repeating the steps (a)-(b) for several cycles, e.g., 2-80 cycles, 2-50 cycles, 2-40 cycles, 10-80 cycles, 10-50 cycles, 10-40 cycles, 20-80 cycles, 20-50 cycles, 20-40 cycles, 30-60 cycles or 40-60 cycles with denaturation between repeating cycles, and then performing the steps (c)-(e).

The denaturation may be carried out by conventional technologies, including, but not limited to, heating, alkali, formamide, urea and glycoxal treatment, enzymatic methods (e.g., helicase action), and binding proteins. For instance, the melting can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

According to an embodiment, the steps (a)-(e) are performed in a reaction vessel or in separate reaction vessels. For example, the steps (a)-(b), (c)-(d) or (e) may be performed in separate reaction vessels.

According to an embodiment, the steps (a)-(e) may be simultaneously or separately even in a reaction vessel depending on reaction conditions (particularly, temperature). For example the steps (a)-(b) and (c)-(e) may be simultaneously or separately even in a reaction vessel depending on reaction conditions (particularly, temperature).

According to an embodiment, the selective amplification using the amplification blocker and the primer pair comprising the upstream primer and the downstream primer, and the detection of the target nucleotide variation using cleavage of the PTO-NV may be separately performed in separate reaction vessels or even in a reaction vessel depending on reaction conditions (particularly, temperature).

Where conducted in separate reaction vessels, the PTO-NV may be cleaved independent on an upstream oligonucleotide, or dependent on an upstream probe.

The present invention does not require that target nucleic acid sequences to be detected and/or amplified have any particular sequence or length, including any DNA (gDNA and cDNA) and RNA molecules.

Where a mRNA is employed as starting material, a reverse transcription step is necessary prior to performing annealing step, details of which are found in Joseph Sambrook, et al., Molecular Cloning, A Laboratory Manual, Cold Spring Harbor Laboratory Press, Cold Spring Harbor, N.Y. (2001); and Noonan, K. F. et al., Nucleic Acids Res. 16:10366 (1988). For reverse transcription, a random hexamer or an oligonucleotide dT primer hybridizable to mRNA can be used.

The target nucleic acid sequences which may be detected and/or amplified include any naturally occurring prokaryotic, eukaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid.

The target nucleic acid sequence to be detected by the present invention includes a wide variety of nucleic acid sequences, e.g., sequences in a genome, artificially isolated or fragmented sequences and synthesized sequences (e.g., cDNA sequences and barcode sequences). For instance, the target nucleic acid sequence includes nucleic acid marker sequences for Immuno-PCR (IPCR). IPCR employs conjugates between nucleic acid marker sequences and antibodies together with PCR, which is widely applied for detecting various types of targets including proteins (see Sano et al., Science 258 pp:120-122(1992), U.S. Pat. No. 5,665,539, Niemeyer et al., Trends in Biotechnology 23 pp:208-216 (2005), U.S. Pat. Pub. No. 2005/0239108 and Ye et al., Journal of Environmental Science 22 pp:796-800(2010)).

The advantages of the present invention may be highlighted in the simultaneous (multiplex) detection of at least two types of nucleotides variations.

According to an embodiment, the method is performed to detect at least two types (more preferably, at least three types, still more preferably at least five types) of nucleotides variations; wherein the upstream primer and the downstream primer comprise at least two types (more preferably, at least three types, still more preferably at least five types) of upstream primers and downstream primers, the amplification blocker comprises at least two types (more preferably, at least three types, still more preferably at least five types) of amplification blockers, and the PTO-NV comprises at least two types (more preferably, at least three types, still more preferably at least five types) of PTO-NVs.

Nucleotide Variation Detection Using Immobilized Oligonucleotide on a Solid Phase The present invention is also effective in detection of nucleotide variations on a solid phase such as microarray.

According to an embodiment, the present invention is performed on the solid phase and an oligonucleotide (e.g. CTO, SO or HO) is immobilized through its 5'-end or 3'-end onto a solid substrate. In a solid phase, the target signal provided on the solid substrate is measured.

The immobilization of the CTO, SO or HO may be done in two fashions.

In the first fashion, the CTO, SO or HO having been already immobilized on the solid substrate is involved in the reaction steps. In the second fashion, the CTO, SO or HO is involved in a non-immobilized form then immobilized on the solid substrate during the reaction steps.

According to an embodiment, in the solid phase reaction, the single label is not required to possess the capability of generating signals different intensities depending on whether nucleic acid sequences having the single label is in a single strand or a double strand. The single label includes, but not limited to, a chemical label (e.g., biotin), an enzymatic label (e.g., alkaline phosphatase, peroxidase, β-galactosidase and β-glucosidase), a radioisotope label (e.g., $I^{125}$ and $C^{14}$), a fluorescent label, a luminescent label, a chemiluminescent label, and a metal label (e.g., gold).

For the solid phase reaction, the CTO, SO or HO is immobilized directly or indirectly (preferably indirectly) through its 5'-end or 3'-end (preferably the 3'-end) onto the surface of the solid substrate. Furthermore, the CTO, SO or HO may be immobilized on the surface of the solid substrate in a covalent or non-covalent manner. Where the immobilized oligoncleotides are immobilized indirectly onto the surface of the solid substrate, suitable linkers are used. The linkers useful in this invention may include any linkers utilized for probe immobilization on the surface of the solid substrate. For example, alkyl or aryl compounds with amine functionality, or alkyl or aryl compounds with thiol functionality serve as linkers for immobilization. In addition, poly (T) tail or poly (A) tail may serve as linkers and significantly decrease space hindrance that is an inhibitory factor to enzymatic actions (e.g., enzymatic cleavage reactions), contributing to increase in hybridization efficiency. The poly (T) tail or poly (A) tail as linkers is not considered a sequence of probes.

According to an embodiment, the CTO, SO or HO may be immobilized on the solid substrate via interaction between binding partners (e.g., biotin/streptavidin). For example, the CTO, SO or HO with one of binding partners (biotin and streptavidin) may be immobilized on the solid substrate whose surface is modified with the other binding partner.

According to an embodiment, the CTO, SO or HO may be immobilized on the solid substrate by a nucleotide sequence for immobilization. For example, the solid substrate whose surface is modified with the nucleotide sequence for immobilization may be used to immobilize the CTO, SO or HO with additional sequence complementary to the nucleotide sequence for immobilization.

According to an embodiment, the solid substrate used in the present invention is a microarray. The microarray to provide a reaction environment in this invention may include any those known to one of skill in the art. All processes of the present invention, i.e., hybridization to target nucleic acid sequences, cleavage, extension, melting and fluorescence detection, are carried out on the microarray. The immobilized oligonucleotides on the microarray serve as hybridizable array elements. The solid substrate to fabricate microarray includes, but not limited to, metals (e.g., gold, alloy of gold and copper, aluminum), metal oxide, glass, ceramic, quartz, silicon, semiconductor, $Si/SiO_2$ wafer, germanium, gallium arsenide, carbon, carbon nanotube, polymers (e.g., polystyrene, polyethylene, polypropylene and polyacrylamide), sepharose, agarose and colloids. The solid substrate may be in the form of a dipstick, a plate, a particle (e.g., bead), an affinity column and a membrane. A plurality of immobilized oligonucleotides in this invention may be immobilized on an addressable region or two or more addressable regions on a solid substrate that may comprise 2-1,000,000 addressable regions. Immobilized oligonucleotides may be fabricated to produce array or arrays for a given application by conventional fabrication technologies such as photolithography, ink-jetting, mechanical microspotting, and derivatives thereof.

The present invention performed on the solid phase can detect simultaneously a plurality of target nucleic acid sequences even using a single type of a label because the labels on the oligonucleotides immobilized are physically separated. In this regard, the number of target nucleic acid sequences to be detected by the present invention on the solid phase is not limited.

Using confocal detection devices, the signal only on the solid substrate may be detected without influence of labels suspended in a liquid phase.

Kits for Detection of Target Nucleotide Variation

In another aspect of this invention, there is provided a kit for detecting a target nucleotide variation on a target nucleic acid sequence using amplification blocker and VD-PTOCE assay, comprising:
(a) a primer pair comprising an upstream primer and a downstream primer for amplification of the target nucleic acid; wherein each of the upstream primer and the downstream primer comprise a hybridizing nucleotide sequence complementary to the target nucleic acid sequence;
(b) an amplification blocker having the resistance to 5' nuclease cleavage; wherein the amplification blocker comprises a complementary sequence to a non-target nucleotide variation which is different from the target nucleotide variation on the target nucleic acid sequence; and
(c) a PTO-NV (Probing and Tagging Oligonucleotide for Nucleotide Variation); wherein and the PTO-NV comprises (i) a 3'-targeting portion comprising a hybridizing nucleotide sequence complementary to the target nucleic acid sequence, (ii) a 5'-tagging portion comprising a nucleotide sequence non-complementary to the target nucleic acid sequence, and (iii) a nucleotide variation discrimination site, comprising a complementary sequence to the target nucleotide variation on the target nucleic acid, positioned on a 5'-end part of the 3'-targeting portion;
(d) a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO-NV and (ii) a templating portion comprising a nucleotide sequence non-complementary to the 5'-tagging portion and the 3'-targeting portion of the PTO-NV; wherein the first fragment or the second fragment released from the PTO-NV is hybridized with the capturing portion of the CTO;

wherein the amplification blocker is hybridized with the target nucleic acid sequence having the non-target nucleotide variation and not hybridized with the target nucleic acid sequence having the target nucleotide variation; wherein the 3'-targeting portion of the PTO-NV is hybridized with the target nucleic acid sequence and the 5'-tagging portion the PTO-NV is not hybridized with the target nucleic acid sequence;

wherein the upstream primer is located upstream of the PTO-NV; the amplification blocker is located downstream of the upstream primer or the downstream primer; and the amplification blocker and the PTO-NV are located between the upstream primer or the downstream primer;

wherein the upstream primer induces through its extended strand the cleavage of the PTO-NV by the enzyme having the 5' nuclease activity; wherein the hybridization of the amplification blocker to the target nucleic acid sequence having the non-target nucleotide variation inhibits the extension of the primer located upstream of the amplification blocker, resulting in blocking the amplification of the target nucleic acid sequence having the non-target nucleotide variation;

wherein when the PTO-NV is hybridized with the target nucleic acid sequence having the target nucleotide variation complementary to the nucleotide variation discrimination site, the 5'-end part of the 3'-targeting portion forms a double strand with the target nucleic acid sequence to induce cleavage from a first initial cleavage site and a first fragment is released; wherein when the PTO-NV is hybridized with the target nucleic acid sequence having the non-target nucleotide variation non-complementary to the nucleotide variation discrimination site, the 5'-end part of the 3'-targeting portion does not form a double strand with the target nucleic acid sequence to induce cleavage from a second initial cleavage site located downstream of the first initial cleavage site and a second fragment is released; wherein the second fragment comprises an additional 3'-end portion allowing the second fragment different from the first fragment;

wherein when the first fragment is hybridized with the capturing portion of the CTO, it is extended to form an extended strand comprising a extended sequence complementary to the templating portion of the CTO; wherein when the second fragment is hybridized with the capturing portion of the CTO, it is not extended.

Since the kit of this invention is constructed to perform the detection method of the present invention described above, the common descriptions between them are omitted in order to avoid undue redundancy leading to the complexity of this specification.

According to an embodiment, the kit further comprises the enzyme having the 5' nuclease activity, a template-dependent nucleic acid polymerase or their combination.

According to an embodiment, the amplification blocker comprises nucleosides/nucleotides having a backbone resistant to the 5' nuclease activity.

According to an embodiment, the amplification blocker comprises peptide nucleic acid (PNA), locked nucleic acid (LNA), Morpholino, glycol nucleic acid (GNA), threose nucleic acid (TNA)), bridged nucleic acids (BNA), N3'-P5' phosphoramidate (NP) oligomers, minor groove binder-linked-oligonucleotides (MGB-linked oligonucleotides), phosphorothioate (PS) oligomers, $C_1$-$C_4$ alkylphosphonate oligomers, phosphoramidates, β-phosphodiester oligonucleotides, a-phosphodiester oligonucleotides or combination thereof.

According to an embodiment, the CTO has a sequence selected such that the CTO is not hybridized with the additional 3'-end portion of the second fragment to prevent the second fragment from extension when the second fragment is hybridized with the capturing portion of the CTO.

According to an embodiment, the nucleotide variation discrimination site is located within 10 nucleotides apart from the 5'-end of the 3'-targeting portion of the PTO-NV.

According to an embodiment, the 5'-end part of the 3'-targeting portion of the PTO-NV comprises a non-base pairing moiety located within 1-5 nucleotides apart from the nucleotide variation discrimination site; wherein the non-base pairing moiety enhances differentiation between the first initial cleavage site and the second initial cleavage site.

According to an embodiment, the non-base pairing moiety is (i) a nucleotide comprising an artificial mismatch base, a non-base pairing base modified to be incapable of base pairing or a universal base, (ii) a non-base pairing nucleotide modified to be incapable of base pairing, or (iii) a non-base pairing chemical compound.

According to an embodiment, the nucleotide variation is a substitution variation, a deletion variation or an insertion variation.

According to an embodiment, the extended strand of the first fragment and the CTO form an extended duplex; wherein the extended duplex has a $T_m$ value adjustable by (i) a sequence and/or length of the first fragment, (ii) a sequence and/or length of the CTO or (iii) the sequence and/or length of the first fragment and the sequence and/or length of the CTO; wherein the extended duplex provides a target signal by (i) at least one label linked to the first fragment and/or CTO, (ii) a label incorporated into the extended duplex during the extension reaction, (iii) at least one label linked to the first fragment and/or CTO and a label incorporated into the extended duplex during the extension reaction or (iv) intercalating label; and wherein the presence of the extended strand is detected by measuring the target signal from the extended duplex in accordance with a melting analysis or a hybridization analysis for the extended duplex.

According to an embodiment, the extended strand of the first fragment and the CTO form an extended duplex; wherein the extended duplex has a $T_m$ value adjustable by (i) a sequence and/or length of the first fragment, (ii) a sequence and/or length of the CTO or (iii) the sequence and/or length of the first fragment and the sequence and/or length of the CTO; wherein the extended duplex provides a target signal by (i) at least one label linked to the first fragment and/or CTO, (ii) a label incorporated into the extended duplex during the extension reaction, (iii) at least one label linked to the first fragment and/or CTO and a label incorporated into the extended duplex during the extension reaction or (iv) intercalating label; and wherein the presence of the extended strand is detected by measuring the target signal from the extended duplex at a pre-determined temperature sufficient to maintain a double strand of the extended duplex.

According to an embodiment, the kit further comprises a signaling oligonucleotide (SO) to detect the extended strand of the first fragment; wherein the SO comprises a complementary sequence to the extended strand and at least one label; the SO provides a detectable signal by association with or dissociation from the extended strand. According to an embodiment, the detectable signal is provided by (i) the label linked to the SO, (ii) a combination of the label linked to the SO and a label linked to the fragment from the PTO-NV, (iii) a combination of the label linked to the SO and a label to be incorporated into the extended strand during the extension reaction, or (iv) a combination of the label linked to the SO and an intercalating dye. According to an embodiment, the kit uses an additional SO comprising a complementary sequence to the extended strand, the two SOs are hybridized with the extended strand in an adjacent manner, the two SOs each comprises one label among a reporter molecule and a quencher molecule of an interactive dual label.

According to an embodiment, the kit further comprises a HO (hybridizing oligonucleotide) to detect the extended strand of the first fragment; wherein the HO comprises a hybridizing nucleotide sequence complementary to the CTO and at least one label; wherein the extension of the first fragment induces the cleavage of the HO by an enzyme having a 5' nuclease activity to generate a detectable signal from the label. According to an embodiment, the detectable signal is provided by (i) an interactive dual label linked to the HO, or (ii) one of an interactive dual label comprising a reporter molecule and a quencher molecule linked to the HO and the other linked to the CTO.

According to an embodiment, the amplification blocker, PTO-NV, CTO, SO and/or HO is blocked at its 3'-end to prohibit its extension.

According to an embodiment, the kit is performed to detect at least two types of nucleotides variations; wherein the upstream primer and the downstream primer comprise at least two types of upstream primers and downstream primers, the amplification blocker comprises at least two types of amplification blockers, and the PTO-NV comprises at least two types of PTO-NVs.

According to an embodiment, the template-dependent nucleic acid polymerase is the same as the enzyme having the 5' nuclease activity.

According to an embodiment, the enzyme having the 5' nuclease activity is a thermostable DNA polymerase having a 5' nuclease activity or FEN nuclease.

All of the present kits described hereinabove may optionally include the reagents required for performing target amplification PCR reactions (e.g., PCR reactions) such as buffers, DNA polymerase cofactors, and deoxyribonucleotide-5-triphosphates. Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The kits, typically, are adopted to contain the constituents aforedescribed in separate packaging or compartments.

The features and advantages of this invention will be summarized as follows:

(a) The present invention is an improvement of a VD-PTOCE assay developed by the present inventors, which aims to effective detection of minor alleles in low-abundance.

(b) The present invention is significantly effective in the detection of a minority mutation in an excess of wild-type DNA. The amplification blocker may restrict the consumption of the PTO-NV on the wild-type DNA by the selective amplification of the mutant DNA. Or, the amplification blocker may compete with the PTO-NV for the hybridization to the wild-type DNA, which prevent the cleavage of the PTO-NV on the wild-type DNA.

(c) According to the present invention, the probe (PTO-NV) shows distinctly different hybridization patterns depending on the presence of the nucleotide variation of interest.

(d) Such distinct hybridization patterns on the nucleotide variation of interest are responsible for differences in initial cleavage sites of the PTO-NV, thereby producing two types of PTO-NV fragments to give signal differentiation depending on the presence of the nucleotide variation of interest.

(e) It is noteworthy that the sequence of the 5'-tagging portion of PTO-NV and the sequence of CTO can be selected with no consideration of target nucleic acid sequences. This makes it possible to pre-design a pool of sequences for the 5'-tagging portion of PTO-NV and CTO. Although the 3'-targeting portion of the PTO-NV has to be prepared with considering target nucleic acid sequences, the CTO can be prepared in a ready-made fashion with no consideration or knowledge of target nucleic acid sequences. Such features provide prominent advantages in multiple target detection, inter alia, on a microarray assay using CTOs immobilized onto a solid substrate.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Detection of a Minority Mutation by a VD-PTOCE Assay with an Amplification Blocker We examined whether the combination of the amplification blocker and the VD-PTOCE assay allows identifying a minority mutation in an excess of wild-type DNA.

Taq DNA polymerase having a 5' nuclease activity was used for the extension of upstream primer and downstream primer, the cleavage of PTO-NV and the extension of PTO-NV fragment. The PTO-NV, amplification blocker and CTO are blocked with a carbon spacer at their 3'-ends to prohibit their extension. BRAF (V600E) wild-type (T) and mutant (A) human genomic DNAs were used as target nucleic acid sequences. The mutant DNA was corresponding to a target nucleic acid sequence having the target nucleotide variation and the wild-type DNA to a target nucleic acid sequence having the non-target nucleotide variation. A series of mixtures having different ratios of mutant and wild-type BRAF DNAs were prepared (mutant 100%, 10%, 1%, 0.1% and 0%) to examine the effect of amplification blocker.

PTO-NV has no labels. The nucleotide variation discrimination site of PTO-NV has a nucleotide (T) complementary to mutant (A) DNA of sense strand (SEQ ID NO: 3). The amplification blocker includes LNA nucleotides and the nucleotide variation discrimination site of the amplification blocker has a nucleotide (T) complementary to wild-type (A) DNA of anti-sense strand (SEQ ID NO: 4).

In VD-PTOCE assay of this Example, the presence of the extended strand produced depending on the presence of the target nucleotide variation (i.e., mutant DNA) was detected by melting analysis of the extended duplex formed with the extended strand and CTO.

CTO is labeled with a quencher molecule (BHQ-2) and a fluorescent reporter molecule (Cal Fluor Red 610) in its templating portion (SEQ ID NO: 5).

The sequences of upstream primer, downstream primer, PTO-NV, amplification blocker and CTO used in this Example are:

```
BRAF-F
                                              (SEQ ID NO: 1)
5'-CTTCATAATGCTTGCTCTGATAGGIIIIIGAGATCTACT-3'

BRAF-R
                                              (SEQ ID NO: 2)
5'-ATAGCCTCAATTCTTACCATCCAIIIIITGGATCCAGA-3'

BRAF-PTO-NV
                                              (SEQ ID NO: 3)
5'-GGTGGACTTGCGGTCTGTAGCTAGACCAAAATCACCTATTTTTACT
GTG[C3 spacer]-3'

Amplification blocker
                                              (SEQ ID NO: 4)
5'-CAGTGAAATCTGGATGG[C3 spacer]-3'

BRAF-CTO-1
                                              (SEQ ID NO: 5)
5'-[BHQ-2]TTTTTTTTGAGCCAGAGTTA[T(Cal Fluor Red
610)]GGTCACCGCAAGTCCACC[C3 spacer]-3'
```

(I: Deoxyinosine)
(Underlined letters indicate the 5'-tagging portion of PTO-NV)
(Bold letter indicates the nucleotide discrimination site)
(Boxed letters indicate LNA nucleotides)

The reaction was conducted in the final volume of 20 µl containing 100 ng of different mixture ratios of BRAF (V600E) mutant (A) and wild-type (T) human genomic DNAs (mutant 100%, 10%, 1%, 0.1% and 0%), 10 pmole of upstream primer (SEQ ID NO: 1), 10 pmole of downstream primer (SEQ ID NO: 2), 5 pmole of PTO-NV (SEQ ID NO: 3), 5 pmole of amplification blocker (SEQ ID NO: 4), 1 pmole of CTO (SEQ ID NO: 5), and 10 µl of 2X Master Mix [containing 2.5 mM $MgCl_2$, 200 µM of dNTPs and 1.6 units of Taq DNA polymerase (Solgent, Korea)]; the tube containing the reaction mixture was placed in the real-time thermocycler (CFX96, Bio-Rad); the reaction mixture was denatured for 15 min at 95° C. and subjected to 50 cycles of 30 sec at 95° C., 60 sec at 60° C. After the reaction, melting curve was obtained by cooling the reaction mixture to 55° C., holding at 55° C. for 10 min, and heating slowly at 55° C. to 85° C. The fluorescence was measured continuously during the temperature rise to monitor dissociation of double-stranded DNAs. Melting peak was derived from the melting curve data.

Figure 8A:
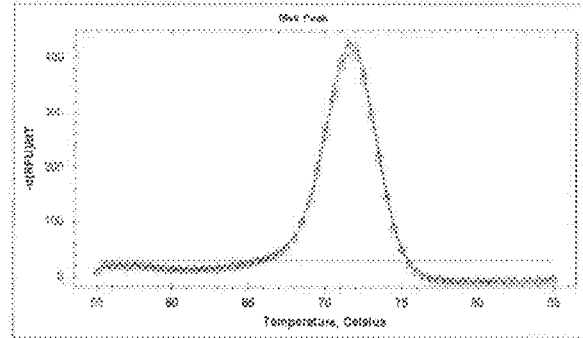
Figure 8A:
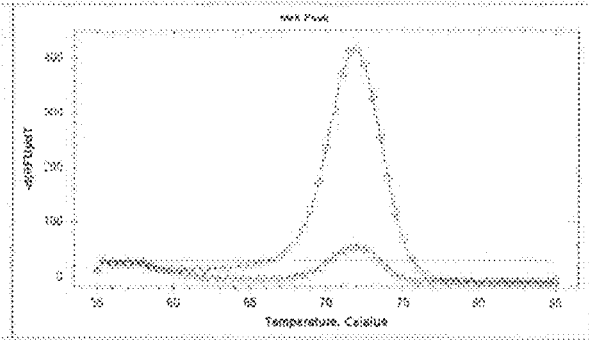
Figure 8A:
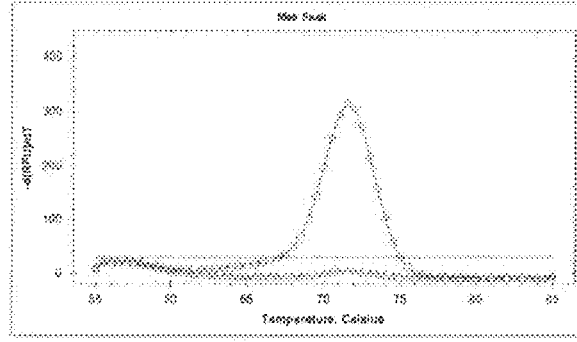
Figure 8A:
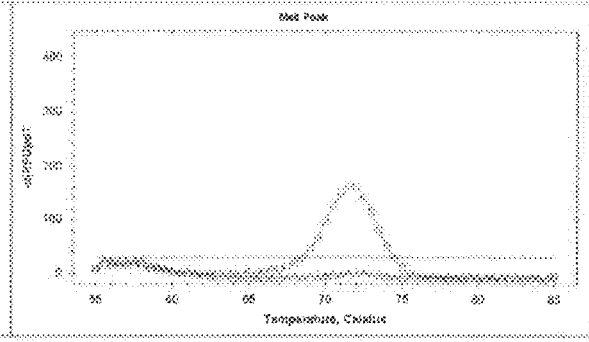
Figure 8A:
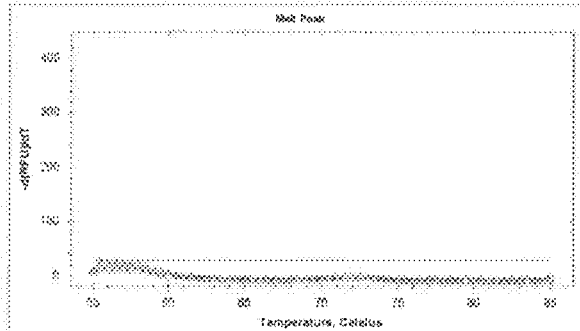
Figure 8A:
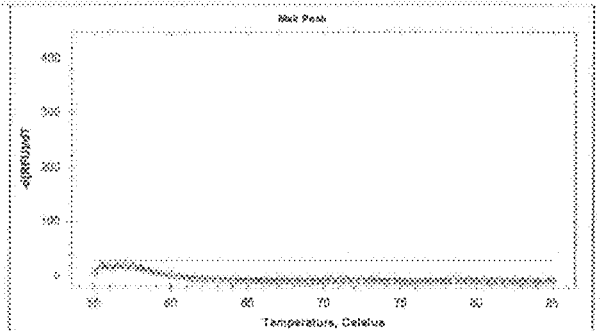

As shown FIGS. 8A and 8B, in the presence of the target nucleic acid sequences, the peaks corresponding to the expected Tm value of the extended duplexes were detected up to 10% of mutant ratio in VD-PTOCE assay without the amplification blocker, but up to 0.1% of mutant ratios with the amplification blocker. No peaks were detected in the absence of any targets.

This results show that the use of the amplification blocker improves the ability of VD-PTOCE assay to identify a minority mutation in an excess of wild-type DNA.

Example 2: Detection of a Minority Mutation by a VD-PTOCE Assay Using a Signaling Oligonucleotide with an Amplification Blocker We further examined whether the combination of the amplification blocker and the VD-PTOCE assay using signaling oligonucleotide (SO) allows identifying a minority mutation in an excess of wild-type DNA.

In VD-PTOCE assay of this Example, the presence of the extended strand produced depending on the presence of the target nucleotide variation (i.e., mutant DNA) was detected by using the signaling oligonucleotide (SO) which specifically hybridized with the extended strand. The hybrid between the extended strand and the SO was used for melting analysis.

Primers, amplification blocker, PTO-NV, BRAF human genomic DNA and Taq DNA polymerase were used as Example 1.

CTO has no label (SEQ ID NO: 6). SO has a quencher molecule (BHQ-2) at its 5'-end and has a fluorescent reporter molecule (Cal Fluor Red 610) at its 3'-end (SEQ ID NO: 7)

The sequences of upstream primer, downstream primer, PTO-NV, amplification blocker, CTO and SO used in this Example are:

```
BRAF-F
                                             (SEQ ID NO: 1)
5'-CTTCATAATGCTTGCTCTGATAGGIIIIIGAGATCTACT-3'
BRAF-R
                                             (SEQ ID NO: 2)
5'-ATAGCCTCAATTCTTACCATCCAIIIIITGGATCCAGA-3'
BRAF-PTO-NV
                                             (SEQ ID NO: 3)
5'-GGTGGACTTGCGGTCTGTAGCTAGACCAAAATCACCTATTTTTACT
GTG[C3 spacer]-3'

Amplification blocker
                                             (SEQ ID NO: 4)
5'-CAGTGAAATCTGGATGG[C3 spacer]-3'

BRAF-CTO-2
                                             (SEQ ID NO: 6)
5'-TTTTTTTTGAGCCAGAGTTATGGTCACCGCAAGTCCACC[C3
spacer]-3'

BRAF-SO
                                             (SEQ ID NO: 7)
5'-[BHQ-2]TTTTTTTTGAGCCAGAGTTATGGTC[Cal Fluor Red
610]-3'
```

(I: Deoxyinosine)
(Underlined letters indicate the 5'-tagging portion of PTO-NV)
(Bold letter indicates the nucleotide discrimination site)
(Boxed letters indicate LNA nucleotides)

The reaction was conducted in the final volume of 20 μl containing 100 ng of different mixture ratios of BRAF (V600E) mutant (A) and wild type (T) human genomic DNAs (mutant 100%, 10%, 1% and 0%), 10 pmole of upstream primer (SEQ ID NO: 1), 10 pmole of downstream primer (SEQ ID NO: 2), 5 pmole of PTO-NV (SEQ ID NO: 3), 5 pmole of amplification blocker (SEQ ID NO: 4), 0.1 pmole of CTO (SEQ ID NO: 6), 3 pmole of SO (SEQ ID NO: 7) and 10 μl of 2X Master Mix [containing 2.5 mM $MgCl_2$, 200 μM of dNTPs and 1.6 units of Taq DNA polymerase (Solgent, Korea)]; the tube containing the reaction mixture was placed in the real-time thermocycler (CFX96, Bio-Rad); the reaction mixture was denatured for 15 min at 95° C. and subjected to 50 cycles of 30 sec at 95° C., 60 sec at 60° C. After the reaction, melting curve was obtained by cooling the reaction mixture to 40° C., holding at 40° C. for 10 min, and heating slowly at 40° C. to 85° C. The fluorescence was measured continuously during the temperature rise to monitor dissociation of an extended strand-SO hybrid. Melting peak was derived from the melting curve data.

Figure 9A:
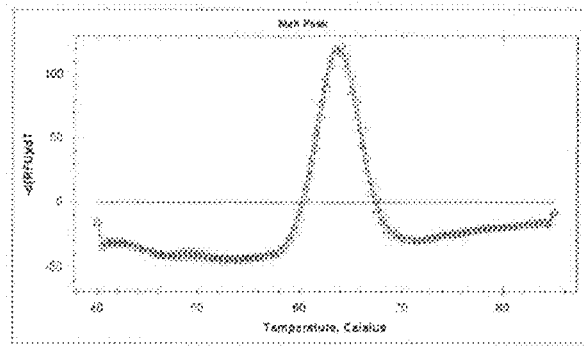
Figure 9A:
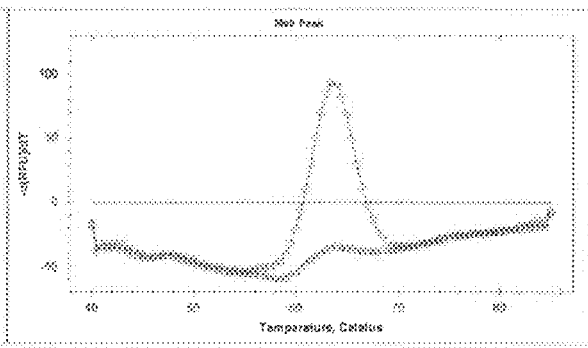
Figure 9A:
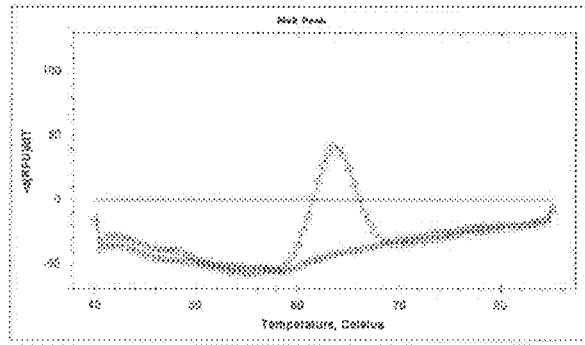
Figure 9A:
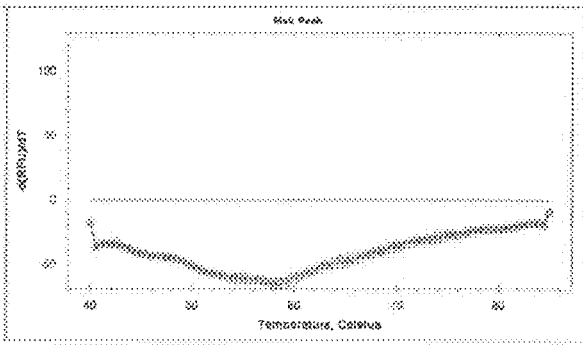
Figure 9A:
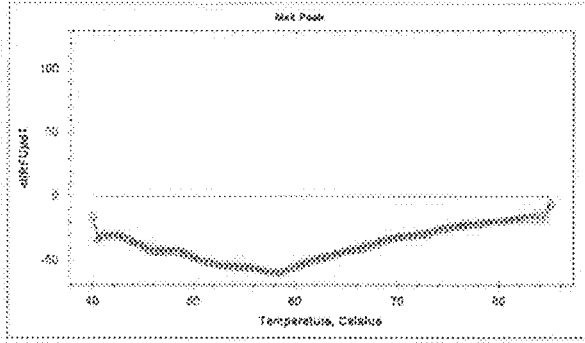

As shown FIGS. 9A and 9B, in the presence of the target nucleic acid sequences, the peak corresponding to the expected Tm value of the extended strand/SO hybrid was detected at 100% of mutant ratio but not at 10% of mutant ratio in VD-PTOCE assay using SO without the amplification blocker. However, the peaks were detected up to 1% of mutant ratio with the amplification blocker. No peaks were detected in the absence of any targets.

This results show that the use of the amplification blocker improves the ability of VD-PTOCE assay using SO to identify a minority mutation in an excess of wild-type DNA.

Example 3: Detection of a Minority Mutation by a VD-PTOCE Assay Using a Hybridization Oligonucleotide with an Amplification Blocker We further examined whether the combination of the amplification blocker and the VD-PTOCE assay using hybridization oligonucleotide (HO) allows identifying a minority mutation in an excess of wild-type DNA.

In VD-PTOCE assay of this Example, the presence of the extended strand produced depending on the presence of the target nucleotide variation (i.e., mutant DNA) was detected by using the hybridization oligonucleotide (HO) which specifically hybridized with the CTO in downstream position than the PTO-NV fragment. During the extension of the PTO-NV fragment on the CTO, the HO is cleaved and provides a signal. The signal generated by the cleavage of HO was detected by real-time detection at a pre-determined temperature in each cycle.

Primers, amplification blocker, PTO-NV, BRAF human genomic DNA and Taq DNA polymerase were used as Example 1.

CTO has no label (SEQ ID NO: 8). HO has a quencher molecule (BHQ-2) at its 5'-end and has a fluorescent reporter molecule (Cal Fluor Red 610) at its 3'-end (SEQ ID NO: 9)

The sequences of upstream primer, downstream primer, PTO-NV, amplification blocker, CTO and HO used in this Example are:

```
BRAF-F
                                           (SEQ ID NO: 1)
5'-CTTCATAATGCTTGCTCTGATAGGIIIIIGAGATCTACT-3'

BRAF-R
                                           (SEQ ID NO: 2)
5'-ATAGCCTCAATTCTTACCATCCAIIIIITGGATCCAGA-3'

BRAF-PTO-NV
                                           (SEQ ID NO: 3)
5'-GGTGGACTTGCGGTCTGTAGCTAGACCAAAATCACCTATTTTTACT
GTG[C3 spacer]-3'

Amplification blocker
                                           (SEQ ID NO: 4)
5'-CAGTGAAATCTGGATGG[C3 spacer]-3'

BRAF-CTO-3
                                           (SEQ ID NO: 8)
5'-TCCGTCCGAGCCAGAGTGATGGTCACCTCACCGCAAGTCCACC[C3
spacer]-3'

BRAF-HO
                                           (SEQ ID NO: 9)
5'-[BHQ-2]GACCATCACTCTGGCTCGGACGGA[Cal Fluor Red
610]-3'
```

(I: Deoxyinosine)
(Underlined letters indicate the 5'-tagging portion of PTO-NV)
(Bold letter indicates the nucleotide discrimination site)
(Boxed letters indicate LNA nucleotides)

The reaction was conducted in the final volume of 20 μl containing 100 ng of different mixture ratios of BRAF (V600E) mutant (A) and wild type (T) human genomic DNAs (mutant 100%, 10%, 1%, 0.1% and 0%), 10 pmole of upstream primer (SEQ ID NO: 1), 10 pmole of downstream primer (SEQ ID NO: 2, 5 pmole of PTO-NV (SEQ ID NO: 3), 5 pmole of amplification blocker (SEQ ID NO: 4), 1 pmole of cm (SEQ ID NO: 8), 3 pmole of HO (SEQ ID NO: 9) and 10 μl of 2X Master Mix [containing 2.5 mM $MgCl_2$, 200 μM of dNTPs and 1.6 units of Taq DNA polymerase (Solgent, Korea)]; the tube containing the reaction mixture was placed in the real-time thermocycler (CFX96, Bio-Rad); the reaction mixture was denatured for 15 min at 95° C. and subjected to 50 cycles of 30 sec at 95° C., 60 sec at 55° C. Detection of the generated signal was performed at the denaturation step (95° C.) of each cycle. The detection at the denaturation temperature (95° C.) supports that the detected signal is provided from the labeled fragment generated by the cleavage of HO.

Figure 10A:
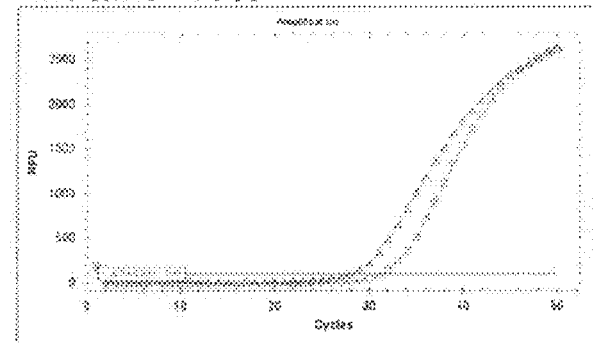
Figure 10A:
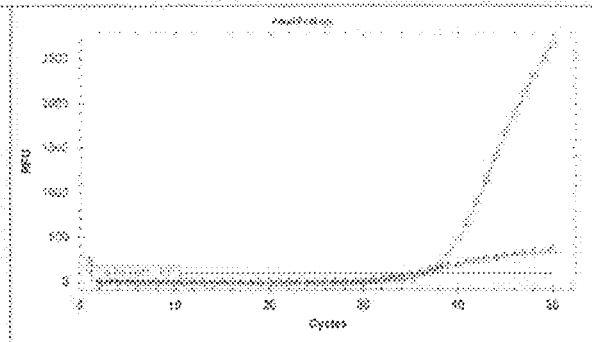
Figure 10A:
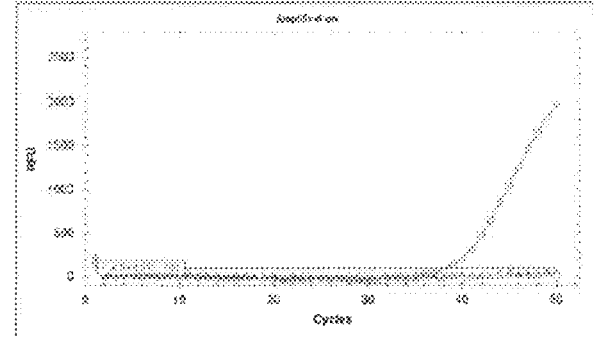
Figure 10A:
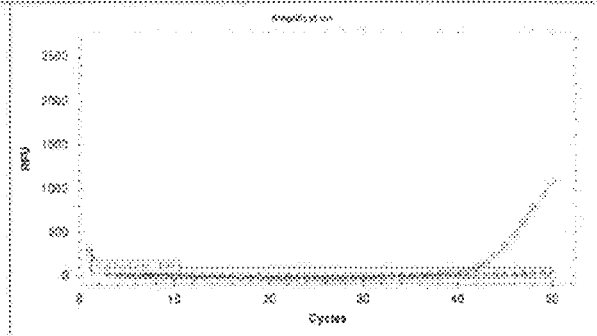
Figure 10A:
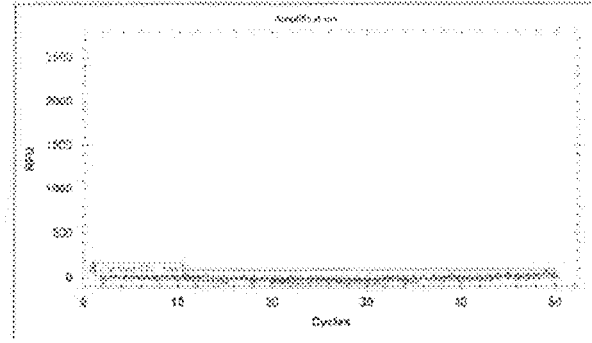
Figure 10A:
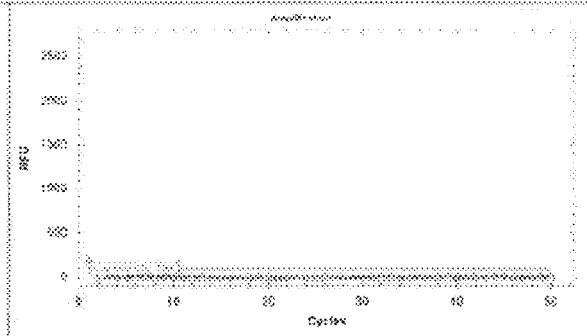

As shown in FIGS. 10A and 10B, in the presence of the target nucleic acid sequences, the fluorescent signal was detected up to 10% of mutant ratio in VD-PTOCE assay using HO without the amplification blocker, but up to 0.1% of mutant ratio with the amplification blocker. No signal was detected in the absence of any targets.

This results show that the use of the amplification blocker improves the ability of VD-PTOCE assay using HO to identify a minority mutation in an excess of wild-type DNA.

Having described a preferred embodiment of the present invention, it is to be understood that variants and modifications thereof falling within the spirit of the invention may become apparent to those skilled in this art, and the scope of this invention is to be determined by appended claims and their equivalents.

---

What is claimed:

1. A method for detecting a target nucleotide variation on a target nucleic acid sequence using an amplification blocker and a VD-PTOCE (Variation Detection by Probing and Tagging Oligonucleotide Cleavage and Extension) assay, comprising:
  (a) hybridizing the target nucleic acid sequence with a primer pair comprising an upstream primer and a downstream primer for amplification of the target nucleic acid, an amplification blocker having the resistance to 5' nuclease cleavage and a PTO-NV (Probing and Tagging Oligonucleotide for Nucleotide Variation); wherein each of the upstream primer and the downstream primer comprises a hybridizing nucleotide sequence complementary to the target nucleic acid sequence; the amplification blocker comprises a complementary sequence to a non-target nucleotide variation different from the target nucleotide variation on the target nucleic acid sequence and the PTO-NV comprises
    (i) a 3'-targeting portion comprising a hybridizing nucleotide sequence complementary to the target nucleic acid sequence,
    (ii) a 5'-tagging portion comprising a nucleotide sequence non-complementary to the target nucleic acid sequence, and
    (iii) a nucleotide variation discrimination site comprising a complementary sequence to the target nucleotide variation on the target nucleic acid, positioned on a 5'-end part of the 3'-targeting portion;
    wherein the amplification blocker is hybridized with the target nucleic acid sequence having the non-target nucleotide variation and not hybridized with the target nucleic acid sequence having the target nucleotide variation; wherein the 3'-targeting portion of the PTO-NV is hybridized with the target nucleic acid sequence and the 5'-tagging portion of the PTO-NV is not hybridized with the target nucleic acid sequence;
    wherein the upstream primer is located upstream of the PTO-NV; the amplification blocker is located downstream of the upstream primer or the downstream primer;
  (b) contacting the resultant of step (a) with an enzyme having 5' nuclease activity under conditions for cleavage of the PTO-NV; wherein the upstream primer induces through its extended strand the cleavage of the PTO-NV by the enzyme having 5' nuclease activity; wherein the hybridization of the amplification blocker with the target nucleic acid sequence having the non-target nucleotide variation inhibits the extension of the primer located upstream of the amplification blocker, thereby blocking the amplification of the target nucleic acid sequence having the non-target nucleotide variation;
    wherein when the PTO-NV is hybridized with the target nucleic acid sequence having the target nucleotide variation complementary to the nucleotide variation discrimination site, the 5'-end part of the 3'-targeting portion forms a double strand with the target nucleic acid sequence to induce cleavage from a first initial cleavage site and a first fragment is released; wherein when the PTO-NV is hybridized with the target nucleic acid sequence having the non-target nucleotide variation non-complementary to the nucleotide variation discrimination site in spite of the presence of the amplification blocker, the 5'-end part of the 3'-targeting portion does not form a double strand with the target nucleic acid sequence to induce cleavage from a second initial cleavage site located downstream of the first initial cleavage site and a second fragment is released; wherein the second fragment comprises an additional 3'-end portion allowing the second fragment to be different from the first fragment;
  (c) hybridizing a fragment released from the PTO-NV with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO-NV and (ii) a templating portion comprising a nucleotide sequence non-complementary to the 5'-tagging portion and the 3'-targeting portion of the PTO-NV; wherein the CTO has a sequence selected such that the CTO is not hybridized with the additional 3'-end portion of the second fragment to prevent the second fragment from extension when the second fragment is hybridized with the capturing portion of the CTO; wherein the first fragment or the second fragment released from the PTO-NV is hybridized with the capturing portion of the CTO;
  (d) performing an extension reaction using the resultant of step (c) and a template-dependent nucleic acid polymerase; wherein when the first fragment is hybridized with the capturing portion of the CTO, it is extended to form an extended strand comprising a extended sequence complementary to the templating portion of the CTO; wherein when the second fragment is hybridized with the capturing portion of the CTO, it is not extended; and
  (e) detecting the presence of the extended strand, whereby the presence of the extended strand indicates the presence of the target nucleotide variation.

2. The method according to claim 1, wherein the amplification blocker comprises nucleosides/nucleotides having a backbone resistant to 5' nuclease activity.

3. The method according to claim 1, wherein the amplification blocker comprises peptide nucleic acid (PNA), locked nucleic acid (LNA), Morpholino, glycol nucleic acid (GNA), threose nucleic acid (TNA), bridged nucleic acids (BNA), N3'-P5' phosphoramidate (NP) oligomers, minor groove binder-linked oligonucleotides (MGB-linked oligonucleotides), phosphorothioate (PS) oligomers, C1-C4 alkylphosphonate oligomers, phosphoramidates, β-phosphodiester oligonucleotides, α-phosphodiester oligonucleotides or a combination thereof.

4. The method according to claim 1, wherein the nucleotide variation discrimination site is located within 10 nucleotides from the 5'-end of the 3'-targeting portion of the PTO-NV.

5. The method according to claim 1, wherein the 5'-end part of the 3'-targeting portion of the PTO-NV comprises a non-base pairing moiety located within 1-5 nucleotides from the nucleotide variation discrimination site; wherein the non-base pairing moiety enhances differentiation between the first initial cleavage site and the second initial cleavage site.

6. The method according to claim 5, wherein the non-base pairing moiety is (i) a nucleotide comprising an artificial mismatch base or a universal base, (ii) a non-base pairing nucleotide modified to be incapable of base pairing, or (iii) a non-base pairing chemical compound.

7. The method according to claim 1, wherein the nucleotide variation is a substitution variation.

8. The method according to claim 1, wherein the amplification blocker, PTO-NV and/or CTO is blocked at its 3'-end to prohibit its extension.

9. The method according to claim 1, wherein the method further comprises repeating all or some of steps (a)-(e) with denaturation between repeating cycles.

10. The method according to claim 1, wherein the method is performed to detect at least two types of nucleotide variations; wherein the upstream primer and the downstream primer comprise at least two types of upstream primers and downstream primers, the amplification blocker comprises at least two types of amplification blockers, and the PTO-NV comprises at least two types of PTO-NVs.

11. The method according to claim 1, wherein step (b) uses a template-dependent nucleic acid polymerase for the extension of the primers; wherein the template-dependent nucleic acid polymerase is the same as the enzyme having 5' nuclease activity.

12. The method according to claim 1, wherein step (b) uses a template-dependent nucleic acid polymerase for the extension of the primers; wherein the template-dependent nucleic acid polymerase is different from the enzyme having 5' nuclease activity.

13. The method according to claim 1, wherein the enzyme having 5' nuclease activity is a thermostable DNA polymerase having 5' nuclease activity or FEN nuclease.

* * * * *